United States Patent [19]

Hider et al.

[11] Patent Number: 4,650,793

[45] Date of Patent: Mar. 17, 1987

[54] IRON-PYRIDONE COMPLEXES FOR ANEMIA

[75] Inventors: Robert C. Hider, St. Osyth, Clacton; George Kontoghiorghes; Jack Silver, both of London; Michael A. Stockham, Saffron Walden, all of England

[73] Assignee: National Research Development Corporation, London, England

[21] Appl. No.: 592,543

[22] Filed: Mar. 22, 1984

[30] Foreign Application Priority Data

Mar. 24, 1983 [GB] United Kingdom ................. 8308055

[51] Int. Cl.$^4$ .................. C07D 213/69; A61K 31/555
[52] U.S. Cl. .................................... 514/188; 514/814; 546/6
[58] Field of Search ............................ 546/6; 424/245

[56] References Cited

FOREIGN PATENT DOCUMENTS

A2118176 10/1983 United Kingdom .
A2117766 10/1983 United Kingdom .

OTHER PUBLICATIONS

Mentasti et al, Chemical Abstracts, 1977, vol. 87, No. 157681s and Mentasti Annali di Chimica, 1976, vol. 66, pp. 401–415.
Howlin et al, Chemical Abstracts, 1982, vol. 97, No. 173875v and Howlin J. Chem. Soc. Dalton Trans., 1982, pp. 1433–1438.
Pitt and Gupta, Development of Iron Chelators for Clinical Use, Anderson and Hiller (Editors), 1975, p. 137, (Symposium Proceedings, Bethesda, Md., 9-2-2-75).
Ward and Harris, Australian Journal of Biological Sciences, 1976, 29, p. 189.
Tamhina and Herak, Croatica Chemica Acta CCA-CAA, 1973, 45, p. 603.
Yasue et al, Yakugaku Zasshi (Journal of Pharmacology), 1970, 90, p. 1222, (and translation).
Berson et al, Journal of the American Chemical Society, 1956, 78, p. 622.
Hare et al, Journal of Medicinal Chemistry, vol. 17, No. 1, Jan. 1974, pp. 1–5.
Bartulin, Chemical Abstracts, vol. 97, 1982, p. 748, No. 92048a, Columbus, Ohio, USA; 122–124.
Bartulin, Bol. Soc. Chil. Quim, 27, 122–124, (1982), (and translation).
Hashiguchi et al., Molecular Pharm., 13, 362–367, (1977).

Primary Examiner—Mark L. Berch
Attorney, Agent, or Firm—Oblon, Fisher, Spivak, McClelland & Maier

[57] ABSTRACT

Pharmaceutical compositions containing an iron complex of a 3-hydroxypyrid-2-one or 3-hydroxypyrid-4-one in which the hydrogen atom attached to the nitrogen atom is replaced by an aliphatic acyl group, by an aliphatic hydrocarbon group, or by an aliphatic hydrocarbon group substituted by one or, except in the case of ionizable groups, more than one substituent selected from aliphatic acyl, alkoxy, aliphatic amine, aliphatic amide, carboxy, aliphatic ester, halogen, hydroxy and sulpho groups and, optionally, in which one or more of the hydrogen atoms attached to ring carbon atoms are replaced by one of said substituents, by an aliphatic hydrocarbon group, or by an aliphatic hydrocarbon group substituted by an alkoxy, aliphatic ester, halogen or hydroxy group, but excluding compounds in which said replacement of hydrogen atoms in the compound is effected only by aliphatic hydrocarbon groups, are of value for the treatment of iron deficiency anemia.

41 Claims, No Drawings

IRON-PYRIDONE COMPLEXES FOR ANEMIA

BACKGROUND OF THE INVENTION

1. Field of the Invention

This invention relates to iron compounds for use in pharmaceutical compositions for the treatment of iron deficiency anaemia.

2. Description of the Background

An adequate supply of iron to the body is an essential requirement for tissue growth in both man and animals. Although there is normally an ample amount of iron in the diet, the level of absorption of iron from food is generally low so that the supply of iron to the body can easily become critical under a variety of conditions. Iron deficiency anaemia is commonly encountered in pregnancy and may also present a problem in the newly born, particularly in certain animal species such as the pig. Moreover, in certain pathological conditions there is a mal distribution of body iron leading to a state of chronic anaemia. This is seen in chronic diseases such as rheumatoid arthritis, certain haemolytic diseases and cancer.

Although a wide range of iron compounds is already marketed for the treatment of iron deficiency anaemia, the level of iron uptake by the body from these compounds is often quite low, necessitating the administration of relatively high dosage levels of the compound. The administration of high dose, poorly absorbed, iron complexes may cause siderosis of the gut wall and a variety of side effects such as nausea, vomiting, constipation and heavy malodorous stools.

In UK patent application No. 8230148, now published as Application No. GB 2,117,766A (corresponding to U.S. application Ser. No. 478,494), now U.S. Pat. No. 4,550,101, we describe a group of iron complexes which we have identified as being of particular value for use at relatively low dosage levels in the treatment of iron deficiency anaemia. These compounds consist of iron complexes of 3-hydroxypyrid-2-ones and 3-hydroxypyrid-4-ones in which the nitrogen atom and optionally one or more of the carbon atoms of the ring are substituted by an aliphatic hydrocarbon group, particularly of 1 to 6 carbon atoms. We have now found that the iron complexes of 3-hydroxypyrid-2-ones and 3-hydroxypyrid-4-ones containing other ring substituents are also of particular value in the treatment of such conditions.

SUMMARY OF THE INVENTION

According to the present invention a pharmaceutical composition comprises an iron complex of a 3-hydroxypyrid-2-one or 3-hydroxypyrid-4-one in which the hydrogen atom attached to the nitrogen atom is replaced by an aliphatic acyl group, by an aliphatic hydrocarbon group, or by an aliphatic hydrocarbon group substituted by one or, except in the case of ionisable groups, more than one substituent selected from aliphatic acyl, alkoxy, aliphatic amide, aliphatic amine, carboxy, aliphatic ester, halogen, hydroxy and sulpho groups and, optionally, in which one or more of the hydrogen atoms attached to ring carbon atoms are replaced by one of said substituents, by an aliphatic hydrocarbon group, or by an aliphatic hydrocarbon group substituted by an alkoxy, aliphatic ester, halogen or hydroxy group, but excluding compounds in which said replacement of hydrogen atoms in the compound is effected only by aliphatic hydrocarbon groups, together with a physiologically acceptable diluent or carrier.

DESCRIPTION OF THE PREFERRED EMBODIMENTS

The iron complexes present in the pharmaceutical compositions according to the present invention preferably contain iron in the ferric state. Although the use of complexes containing iron in the ferrous state may be considered, such complexes tend to be less stable and are thus of less interest. The iron complexes are preferably neutral and this is conveniently achieved by complexing with the iron cation the appropriate number of anions derived from a hydroxypyridone (through the conversion $OH \rightarrow O^-$) necessary to produce neutrality. Preferred iron complexes of use in the present invention are thus of the 3:1 form, containing three hydroxypyridone anions complexed with a ferric cation, and complexes of this type are believed never to have been previously prepared. It will be appreciated, however, that the invention does not exclude the use of complexes of the 1:1 or particularly the 2:1 form, usually in association with a physiologically acceptable anion or anions to achieve neutrality, for example the chloride ion.

The ability of both the free compound and its iron complex to permeate membranes is important in the context of the treatment of anaemia and it is also desirable for both to possess some degree of water solubility. A good indication of the physical properties of a compound and its iron complex in this respect is provided by the value of the partition coefficient ($K_{part}$) obtained on partition between n-octanol and tris hydrochloride (20 mM, pH 7.4; tris representing 2-amino-2-hydroxymethylpropane 1,3-diol) at 20° C. and expressed as the ratio (concentration of compound in organic phase)/(concentration of compound in aqueous phase). Preferred compounds show a value of $K_{part}$ for the free compound of above 0.02 or 0.05 but less than 3.0, especially of above 0.2 but less than 1.0, together with a value of $K_{part}$ for the 3:1 hydroxypyridone iron(III) complex of above 0.02 but less than 6.0, especially of above 0.2 but less than 1.0. The following comments upon preferences among the groups used for replacement of hydrogen atoms attached to nitrogen or carbon atoms of the pyridone ring are directed towards the use of compounds having partition coefficients in the free and complexed state which lie in these preferred ranges. For examples of measured partition coefficients of specific compounds reference should be made to Table 1 of Example 1.

Compositions of particular interest are those containing the iron complex of a compound in which the hydrogen atom attached to the nitrogen atom of the pyridone ring is replaced by a group other than an aliphatic hydrocarbon group, although the invention does of course extend to compositions containing a compound in which this hydrogen atom is replaced by an aliphatic hydrocarbon group and a hydrogen atom attached to a carbon atom of the ring is replaced by another type of group. Furthermore, although compounds having a group other than an aliphatic hydrocarbon group attached to the ring nitrogen atom may also have the hydrogen atom of one or more ring carbon atoms replaced by the same or a different group which is also other than an aliphatic hydrocarbon group, it is preferred either that the ring carbon atoms in such compounds are unsubstituted or that substitution is limited to aliphatic hydrocarbon groups.

More than one of the ring carbon atoms of the 3-hydroxypyrid-2-or -4-one may be substituted, for example two of such atoms, either by the same substituent group or by different substituent groups, for example by an aliphatic hydrocarbon group and by another type of substituent, although compounds in which none or only one of the ring carbon atoms are substituted, for example by an aliphatic hydrocarbon group, are preferred. Substitution of these atoms is of more interest with the 3-hydroxypyrid-4-ones, for example at the 6- or particularly the 2-position, than with the 3-hydroxypyrid-2-ones. Particularly when the ring carbon atoms are substituted by the larger groups, however, there may be an advantage in avoiding substitution on a carbon alpha to the

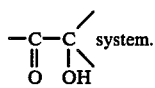 system.

This system is involved in the complexing with iron and the close proximity of one of the larger aliphatic hydrocarbon groups may lead to steric effects which inhibit complex formation.

Where a ring nitrogen or carbon atom is substituted by an aliphatic hydrocarbon group, this group may be cyclic or acyclic, having a branched chain or especially a straight chain in the latter case, and may be unsaturated or especially saturated. Groups of from 1 to 6 carbon atoms, particularly of 1 to 4 and especially of 1 to 3 carbon atoms, are of most interest. Alkyl groups are preferred, for example cyclic groups such as cyclopropyl and especially cyclohexyl but, more particularly preferred are acyclic groups such as methyl, ethyl, n-propyl and isopropyl. Where the ring carbon atoms are substituted by an aliphatic hydrocarbon group or groups these are preferably methyl but in the case of a group substituting the nitrogen atom larger groups may more often be utilised with particular advantage.

In the case of substituted aliphatic hydrocarbon groups, the preferences as to the nature of the aliphatic hydrocarbon group are broadly as expressed above but the preferences as to size are somewhat different. Firstly, in the case of such groups attached to nitrogen, groups containing only 1 carbon atom are of less interest, particularly with certain substituent groups such as hydroxy and amine groups, since compounds containing such substituted groups may be difficult to prepare because of a relative lack of stability of the systems

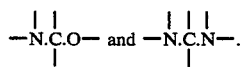

Furthermore, in the case of substituted aliphatic hydrocarbon groups attached both to nitrogen and to carbon atoms, a substituted methyl group containing a hydrophilic substituent may cause the compound to be of too hydrophilic a character unless the effect of this group is balanced by that of another, more hydrophobic, group. For this reason aliphatic hydrocarbon groups of 2 or especially 3 or more carbon atoms are often preferred in this context, particularly where the substituent is an amine, carboxy, hydroxy or sulpho group, although groups of 1 or 2 carbon atoms may be very suitable in certain cases, for example where the substituent is an amide group, particularly an N-substituted one. It will be appreciated therefore, that the range of size of aliphatic hydrocarbon groups which are substituted may conveniently be greater than that indicated above as being preferred for unsubstituted groups, for example 1 to 8 carbon atoms, particularly 1 to 6 carbon atoms, and especially 3, 4 or 5 carbon atoms when the substituted group contains no additional hydrophobic group.

In general, the circumstances in which the smaller substituted aliphatic hydrocarbon groups are of interest occur either when the substituent group involved is not of a particularly hydrophilic character or when it is of such a character but an additional group, such as a larger aliphatic hydrocarbon group of, for example, 3 or more carbon atoms is present to provide a balance to the hydrophilic character. Such a larger group may be present in the same substituted aliphatic hydrocarbon group, as is the case with the amide containing groups referred to above, or separately. In particular, when both the ring nitrogen atom and one or more of the ring carbon atoms carry a substituted aliphatic hydrocarbon group, it may be suitable for one of the substituted aliphatic hydrocarbon groups, for example that carried by the nitrogen atom, to be of a size as discussed above, for example of 3 or 4 to 5 or 6 carbon atoms, and for the other or others to be smaller, for example of 2 or particularly 1 carbon atom. Thus, when the nitrogen atom carries either a substituted aliphatic hydrocarbon group or an acyl group, and also a hydrogen atom or atoms attached to carbon are replaced, then such replacement, for example at the 6-position, as an alternative or in addition to being effected by an aliphatic hydrocarbon group, may conveniently be effected by a substituted methyl group. It will be appreciated that substitution at the nitrogen atom of the compounds is of particular interest in the present invention and that it is preferred to dictate the hydrophilic/hydrophobic balance in the molecule primarily through such N-substitution. It is more usually the case therefore that, when the compounds are C-substituted but the preferred form of C-substitution involving aliphatic hydrocarbon groups is not present, the C-substituent or substituents incorporate substituted aliphatic hydrocarbon groups which are such that preferences as to the size and nature of these groups are broadly as expressed for the unsubstituted groups, for example being substituted alkyl groups of 1 to 3 carbon atoms and particularly substituted methyl groups such as chloromethyl, ethoxymethyl, and especially hydroxymethyl.

Substituted aliphatic hydrocarbon groups attached to the nitrogen atom of iron complexes of compounds of use in the present invention may contain more than one substituent, for example two substituents of a different type. One example of such a multiply substituted aliphatic hydrocarbon group occurs where the group is substituted both by a sulphonic or particularly a carboxylic acid ester group and by a sulphonic or particularly a carboxylic acid amide group. One potential drawback with such multiply substituted groups, however, is their increased size and it is the case, therefore, that groups containing one substituent, often terminally substituted on the aliphatic hydrocarbon group, are more commonly employed and, as indicated hereinbefore, substitution by more than one ionisable group (amine, carboxy or sulpho) is specifically excluded (substitution by more than one group, only one of which is ionisable, is not excluded although not of great interest).

As regards the substituent groups present in the iron complexes of compounds of use in the present invention, an aliphatic acyl group may be a formyl group but alkylcarbonyl groups are of most interest. Such acyl groups may, for example, be of 2 to 4 or 5 carbon atoms, and particularly may contain alkyl groups of the type described above as being preferred as an aliphatic hydrocarbon group substituent at a ring nitrogen or carbon atom being, for example, —COCH$_2$CH$_3$ or especially —COCH$_3$. Alkoxy groups may conveniently be of 1 to 4 carbon atoms and contain similar alkyl groups to those which are preferred in the alkylcarbonyl groups, examples of such substituents being ethoxy and particularly methoxy.

Amine substituents may consist of a group —NH$_2$ or its charged equivalent, a group —N$^{+H}$$_3$, which will be associated with a physiologically acceptable anion, for example a chloride or other halide ion, a solubilising anion such as that from methane sulphonic or isethionic acid, or an anion derived from the hydroxy group of the ring (OH→O$^-$), or such a —NH$_2$ or —N$^{+H}$$_3$ group in which one or more of the hydrogen atoms is replaced by an aliphatic hydrocarbon group, for example an alkyl group such as is described above as a substitutent at a ring nitrogen or carbon atom. Amide substituents may contain a sulphonyl or a carbonyl group. The latter type are, however, of most interest and the further discussion will therefor refer to them although it applies equally to the sulphonyl type. The amide substituent may be of the unsubstituted form —CONH$_2$ or may contain a nitrogen atom which is mono- or di-substituted as just described for the amine substituents, for example being a group —CONHCH$_3$, etc. Alternatively, the

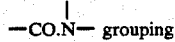 grouping of the amide substituent may be arranged in the opposite sense so that in a N-substitutent, for example, the nitrogen atom of the amide grouping is linked to the aliphatic hydrocarbon group which is attached to the nitrogen atom of the ring, the carbonyl group being attached to an aliphatic hydrocarbon group, for example an alkyl group such as is described above as a substituent at a ring nitrogen or carbon atom, or, in the case of a carboxylic acid amide but not in the case of a sulphonic acid amide, to hydrogen. With such amide groups arranged in this opposite sense, the nitrogen atom may carry a hydrogen atom or be mono-substituted as discussed for amide substituents of the first mentioned form, that form of amide substituent being the one of particular interest.

Carboxy and sulpho substituents may be present as the group —CO$_2$H or —SO$_3$H, or as the anion derived therefrom in combination with a physiologically acceptable cation, for example the cation of an alkali metal such as sodium, quaternary ammonium ions or protonated amines such as the cation derived from tris (tris represents 2-amino-2-hydroxymethyl propane 1,3-diol). Ester substituents may contain a sulphonyloxy or preferably a carbonyloxy group and may be arranged in either sense, i.e. with a carboxylic acid ester the group —CO.O— may have either the carbonyl group or the oxy group linked to the carbon atom of the ring or the nitrogen atom of the ring (through an aliphatic hydrocarbon group on which the ester group is substituted, where appropriate). The other group of oxy and carbonyl will be linked to an aliphatic hydrocarbon group forming part of the ester group or, in the case where this is a carbonyl group may alternatively be linked to hydrogen (this possibility does not apply in the case of sulphonic acid esters). Once again, preferred aliphatic hydrocarbon groups contained by the ester group are those described above as substituents in relation to substitution on a ring nitrogen or carbon atom. In the case of N-substituents, where the ester group is attached to an aliphatic hydrocarbon group which is in turn attached to the ring, ester groups in which the carbonyl or sulphonyl group is linked to this aliphatic hydrocarbon group are preferred, for example the groups —CH$_2$CO$_2$CH$_3$ and —CH$_2$CO$_2$C$_2$H$_5$. In the case of C-substituents the reverse is true and with any C-substituent consisting of an aliphatic hydrocarbon group substituted by an ester group there is a strong preference for the oxy group to be attached to the aliphatic hydrocarbon group which is in turn attached to the ring, for example as in the groups —CH$_2$O.COCH$_3$ and —CH$_2$O.COC$_2$H$_5$. Halogen substituents may conveniently be iodo, fluoro, bromo or especially chloro.

It should be noted that sulphonic acid groups and the corresponding ester and amide groups are of less interest as N-substitutents in the case of the pyrid-2-ones than in that of the pyrid-4-ones but that N-substituents consisting of an aliphatic hydrocarbon group substituted by an acyl group are of most interest in the case of the pyrid-2-ones.

Among the substitutents on the ring nitrogen atom of some particular interest are aliphatic acyl groups and aliphatic hydrocarbon groups substituted by amine, amide, carboxy, aliphatic ester and hydroxy groups, for example the groups —COR$_1$, —(CH$_2$)$_n$—COXR$_2$ and —(CH$_2$)$_m$—XH and to a lesser extent the more complex type of group —(CH$_2$)$_n$CH(COY)NHCOR$_2$, in which R$_1$ is an alkyl group, for example methyl, ethyl or n-propyl, R$_2$ is hydrogen or an alkyl group, for example methyl, ethyl, n-propyl, isopropyl or n-butyl, X is an oxy or imino group, Y is OR$_1$ or NR$_2$, n is an integer from 1 to 4 or 6, particularly 2, 3 or 4, and m is an integer from 2 to 4 or 6, particularly 3, 4 or 5. It will be appreciated that there is an inter-relation between the preferred values of n and R$_2$ so that the groups having the higher values of n tend to have the lower values of R$_2$, and vice versa, so that in groups —(CH$_2$)$_n$—COXR$_2$, for example, —(CH$_2$)$_n$— and R$_2$ may conveniently together contain 3 to 7 carbon atoms, especially 4 to 6 carbon atoms. Also of interest as N-substitutents in the case where a ring carbon atom is substituted by other than an aliphatic hydrocarbon group are aliphatic hydrocarbon groups, for example groups R$_1$, R$_1$ being as described above.

Among substituents on the ring carbon atoms which are of some particular interest are aliphatic hydrocarbon groups and such groups substituted by a halogen, alkoxy or especially a hydroxy group, for example the groups R$_1$, —CH$_2$Cl, —CH$_2$OC$_2$H$_5$ and —CH$_2$OH in which R$_1$ is as described above.

The N-substituents described above may be present on the nitrogen atoms of various 3-hydroxypyrid-2-ones and 3-hydroxypyrid-4-ones, in particularly 3-hydroxypyrid-2-one, 3-hydroxypyrid-4-one, 2-alkyl(e.g. methyl and ethyl)-3-hydroxypyrid-4-ones, 6-alkyl (e.g. methyl)-3-hydroxypyrid-4-ones, 2,6-dialkyl(e.g. dimethyl)-3-hydroxypyrid-4-ones and 3-hydroxy-6-hydroxymethyl-pyrid-4-one. In the case of the 3-hydroxypyrid-2-ones, N-substituent groups of the aliphatic acyl, and amide- or ester-substituted aliphatic hydrocarbon group type are of especial interest whilst in the case of the 3-hydroxypyrid-4-ones, N-substituent groups of the aliphatic acyl and amide-, ester- and hydroxy-substituted aliphatic hydrocarbon group type are of especial interest.

Specific examples of N-substituted 3-hydroxypyrid-2- and -4-ones lacking C-substitution other than by an aliphatic hydrocarbon group are the following compounds, with the various symbols being as defined above and R being hydrogen, ethyl or especially methyl whilst p represents 0, 1, 2, 3 or 4 (the case of $R_2=H$ being of less interest when p=0). Compounds (IV) in which X is an oxy group and compounds (II), and also (V), in which X is an imino group may be mentioned particularly.

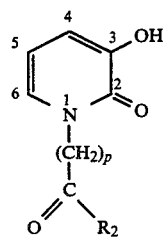 (I)

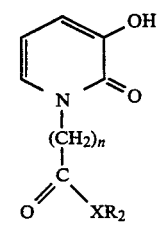 (II)

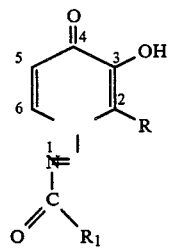 (III)

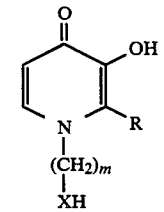 (IV)

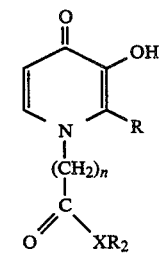 (V)

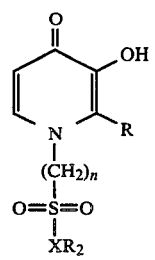 (VI)

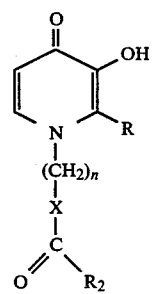 (VII)

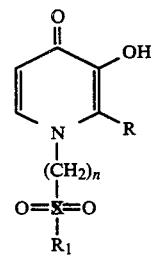 (VIII)

Examples of pyridones containing C-substituents other than aliphatic hydrocarbon groups and N-substituents which are aliphatic hydrocarbon groups are the 1-alkyl-6-halomethyl-3-hydroxypyrid-4-ones and the 1-alkyl-3-hydroxy-6-hydroxymethylpyrid-4-ones and their 6-alkoxymethyl analogues, specific examples of which are the following compounds in which the various symbols are as defined above, the two symbols $R_1$ representing the same or a different alkyl group in (XI), Hal represents a halogen group.

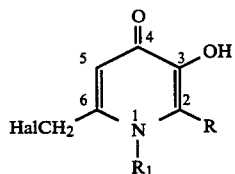 (IX)

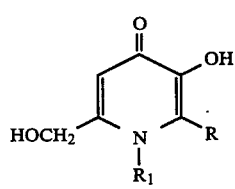 (X)

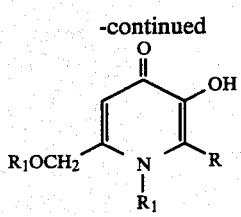

(XI)

It should be noted that among the 3-hydroxypyrid-2-ones and 3-hydroxypyrid-4-ones, the former are of rather greater interest in the iron complex form for iron donation and the latter are of rather greater interest in the free form for iron removal in the treatment of conditions involving iron overload, as described in another UK application of even date herewith.

3-Hydroxy-6-hydroxymethyl-1-methylpyrid-4-one, 1-(2'-aminoethyl)-3-hydroxypyrid-4-one, 3-hydroxy-1-(2'-hydroxyethyl)-2-methylpyrid-4-one, 1-carboxymethyl-3-hydroxy-2-methylpyrid-4-one and 1-ethoxycarbonylmethyl-3-hydroxy-2-methylpyrid-4-one are known compounds but all of the other hydroxypyridones described above are believed to be novel.

The colour reaction which 1-methyl-3-hydroxy-6-hydroxymethylpyrid-4-one shows in solution with ferric chloride has been reported in the literature but no product was characterised. Moreover, it should be noted that the procedure described does not yield a solid complex and that the prevailing conditions are such that the mixture of complexes which would be formed in solution does not include a complex of the 3:1 form referred to hereinbefore, both the amount of ferric chloride and also the pH of the reaction mixture having an influence on the nature of the complex produced.

Subject to the limitations imposed by this prior art, the present invention thus also includes as compounds, per se, an iron complex of a 3-hydroxypyrid-2-one or 3-hydroxypyrid-4-one in which the hydrogen atom attached to the nitrogen atom is replaced by an aliphatic acyl group, by an aliphatic hydrocarbon group, or by an aliphatic hydrocarbon group substituted by one or, except in the case of ionisable groups, by more than one substituent selected from aliphatic acyl, alkoxy, aliphatic amine, aliphatic amide, carboxy, aliphatic ester, halogen, hydroxy and sulpho groups and, optionally, in which one or more of the hydrogen atoms attached to ring carbon atoms are replaced by one of said substituents, by an aliphatic hydrocarbon group, or by an aliphatic hydrocarbon group substituted by an alkoxy, aliphatic ester, halogen or hydroxy group, but excluding compounds in which said replacement of hydrogen atoms is effected only by aliphatic hydrocarbon groups. In particular, the invention includes as compounds, per se, a neutral iron complex containing 1 molar proportion of iron(III) and 3 molar proportions of a 3-hydroxypyrid-2-one or 3-hydroxypyrid-4-one as just defined.

The iron complexes are conveniently prepared by the reaction of the hydroxypyridone and iron ions, the latter conveniently being derived from an iron salt, particularly a ferric halide and especially ferric chloride. The reaction is conveniently effected in a suitable mutual solvent and water may often be used for this purpose. If desired, however, an aqueous/organic solvent mixture may be used or an organic solvent, for example ethanol, methanol, chloroform and mixtures of these solvents together and/or with water where appropriate. In particular, methanol or especially ethanol may be used as the solvent where it is desired to effect the separation of at least a major part of a by-product such as sodium chloride by precipitation whilst the iron complex is retained in solution.

It will be appreciated that the nature of the iron complex obtained by the reaction of a hydroxypyridone and iron ions will depend both on the proportion of these two reactants and upon the pH of the reaction medium. Thus, for the preparation of the 3:1 ferric complex, for example, the hydroxypyridone and the ferric salt are conveniently mixed in solution in a 3:1 molar proportion and the pH adjusted to a value in the range of 6 to 9, for example 7 or 8. If a similar excess of hydroxypyridone:iron is employed but no adjustment is made of the acidic pH which results on the admixture of the hydroxypyridone and an iron salt such as ferric chloride then a mixture of the 2:1 and 1:1 complex will instead be obtained.

Reaction to form the iron complex is generally rapid and will usually have proceeded substantially to completion after 5 minutes at about 20° C., although a longer reaction time may be used if necessary. Following separation of any precipitated by-product, such as sodium chloride in the case of certain solvent systems, the reaction mixture may conveniently be evaporated on a rotary evaporator or freeze dried to yield the solid iron complex. This may, if desired, be crystallised from a suitable solvent, for example water, an alcohol such as ethanol, or a solvent mixture, including mixtures containing an ether. The present invention thus further includes a process for the preparation of an iron complex of a 3-hydroxypyrid-2-one or 3-hydroxypyrid-4-one as defined hereinbefore, which comprises reacting said hydroxypyridone with iron ions and isolating the resultant complex.

Whilst for some uses it may be appropriate to prepare the iron complex in substantially pure form, i.e. substantially free from by-products of manufacture, in other cases, for example with a solid oral formulation as described hereinafter, the presence of by-products such as sodium chloride may be quite acceptable. In general, however, the neutral 3:1 [hydroxypyridone:iron(III)] complex is of particular interest in a form free from by-products which are complexes containing different proportions of hydroxypyridone and iron, in particular the 2:1 and 1:1 complexes. Accordingly the present invention includes an iron complex, for example the 3:1 hydroxypyridone:iron(III) complex, of a 3-hydroxypyrid-2-one or 3-hydroxypyridone-4-one as defined hereinbefore, when in a form substantially free from iron complexes of the hydroxypyridone containing other proportions of iron. As indicated hereinafter, it may be advantageous under some circumstances for the iron complex to be used in admixture with the free hydroxypyridone and, if desired, such a mixture may be obtained directly by reacting a molar proportion of the hydroxypyridone and iron ions of greater than 3:1.

The 3-hydroxy-pyrid-2-one compounds may conveniently be prepared by nucleophilic substitution at the nitrogen atom of the corresponding 2,3-dihydroxypyridine or one containing groups covertible to C-substituents present in the desired pyridone, for example using an organic halide R'X in which R' represents the group present on the nitrogen atom of the desired 3-hydroxypyrid-2-one or a group convertible thereto and X represents a halogen group. In particular, X may for example represent an iodo group when R' represents an aliphatic hydrocarbon group or such a group of 2 or more carbon atoms substituted by an aliphatic acyl group such as $CH_3CO(CH_2)$—, or a bromo group when R' represents an aliphatic acyl group, such as $CH_3CO$— or $CH_3CH_2CO$—, or an aliphatic hydrocarbon group substituted by an aliphatic acyl group, such as $CH_3COCH_2$—, or an aliphatic ester group, such as $C_2H_5OCOCH_2$—. A group of the last mentioned type, once introduced onto the nitrogen atom, may be hydrolysed to yield an aliphatic hydrocarbon group substituted by a carboxy (or sulpho) group, which carboxy (or sulpho) group may in turn be converted to an amide group or even another ester group.

The 3-hydroxypyrid-4-one compounds may conveniently be prepared similarly or preferably from the more readily accessible corresponding 3-hydroxy-4-pyrone or a 3-hydroxy-4-pyrone containing groups convertible to the C-substituent present in the desired pyridone, for example by the reaction $-CH_2OH-\rightarrow-CH_2Hal$. Thus the 3-hydroxy-4-pyrone may conveniently be converted to the 3-hydroxy-pyrid -4-one through protection of the hydroxy groups, for example as an ether group and such as a benzyloxy group, reaction of the protected compound with a compound $R'NH_2$, in which R' represents the group present on the nitrogen atom of the desired 3-hydroxypyrid-4-one or a group convertible thereto, in the presence of a base, for example an alkali metal hydroxide such as sodium hydroxide. The protecting group may then be removed and any other modification of the C-substituents effected. In particular R' may for example represent an aliphatic hydrocarbon group, a hydroxyamine, such as 2-hydroxyethylamine, or 3-hydroxypropylamine, a diamine, such as ethylenediamine, or an amino acid, such as glycine, α- and β-alanine, γ-amino butyric acid or taurine. Hydroxy, amine and carboxy (or sulpho) groups in N-substituents may of course be converted to ester, amide and ester groups, respectively.

An alternative procedure involves the use of a 2-aliphatic acyl 3-hydroxyfuran which may be reacted with a compound $R'NH_2$, the reaction, for example, of 2-acetyl-3-hydroxyfuran with the sodium salt of glycine to form 1-carboxymethyl-3-hydroxy-2-methylpyrid-4-one being described by Severin and Loidl in Z. Lebensm. Unters.-Forsch. 1976, 161, 119.

An example of the modification of C-substituents after formation of the pyridone ring arises in the case where it is appropriate for substituents on carbon atoms of the ring to be protected whilst substitution is effected at the nitrogen atom of the ring. Thus, for example, where a hydroxymethyl group is present on the ring as well as the 3-hydroxy group, both hydroxy groups in a 3-hydroxy-4-pyrone may be protected as described above. Moreover, N-acylated pyrid-4-ones may be prepared by direct acylation but it is preferred to protect the 3-hydroxy group, for example as an ether group such as a benzyloxy group, and to remove this protecting group after the N-acylation has been effected. A similar form of protection of the 3-hydroxy group is suitable where a 6-hydroxyalkyl group is present which is being modified, for example to give a 6-alkoxyalkyl or 6-haloalkyl group.

It will be appreciated from the foregoing that in many cases the final stage in the preparation of the compound comprises deprotecting the hydroxy group of a pyridone having similar ring carbon atom substituents but with the 3-hydroxy group in protected form and either the same ring nitrogen atom substituent or one convertible thereto and, where applicable, converting the N-substitutent to that present in said compound and/or, optionally, converted the compound to a salt thereof containing a physiologically acceptable ion or ions.

Compounds containing substituent groups which are required to be in salt form may be converted to salts by reaction with the appropriate acid or base according to standard procedures (amino substituent compounds of a zwitterion type containing a cation from the amino group and an anion from the 3-hydroxy group may be prepared by crystallisation from aqueous media at a pH of about 9). Conveniently, however, the substituent groups are not present in salt form.

It will be appreciated that these are not the only routes available to these compounds and that various alternatives may be used as will be apparent to those skilled in the art, as will be the routes to the various intermediates required such as C-substituted 2,3- and 3,4-dihydroxypyridines and 3-hydroxy-4-pyrones.

Moreover, it will be appreciated that certain of the compounds may be converted in vivo to other compounds which are responsible for the metal binding activity observed in vivo. This will be true, for example, of compounds containing ester groups which are likely to be converted to carboxy groups when the compounds are administered orally.

The iron complexes may be formulated for use as pharmaceuticals for veterinary, for example in an avian or particularly a mammalian context, or especially for human use by a variety of methods. For instance, they may be applied as an aqueous, oily or emulsified composition incorporating a liquid diluent which most usually will be employed for parenteral administration and therefore may conveniently be sterile and pyrogen free. However, oral administration is generally to be preferred for the treatment of iron deficiency anaemia in humans and the complexes of the present invention may be given by such a route. Although compositions incorporating a liquid diluent may be used for oral administration, it is preferred, particularly in humans, to use compositions incorporating a solid carrier, for example a conventional solid carrier material such as starch, lactose, dextrin or magnesium stearate. Such solid compositions may conveniently be of a formed type, for example as tablets, capsules (including spansules), etc. The iron complex will of course be present in such a preferred composition in solid form and the present invention extends to an iron complex of a 3-hydroxypyrid-2-one or 3-hydroxypyrid-4-one as defined hereinbefore in solid form.

Although solid compositions are preferred in many applications, liquid compositions are of interest in certain particular instances, for example human and veterinary intramuscular administration and veterinary oral administration as discussed hereinafter. It is often desirable, particularly for such oral administration, to produce liquid compositions containing a higher concentration than is readily obtainable with a purely aqueous composition or indeed one containing organic solvents such as simple monohydric alcohols, compositions utilising such diluents therefore being of less interest when not in sterile form. It has been found that higher concentrations may be achieved by the use of solvents containing two or more hydroxy groups or a hydroxy and an ether group, especially glycols or glycol ethers, either in admixture with water or, for better solubilisation, alone. The glycol ethers of particular interest are the mono-ethers containing as an etherifying group an aliphatic hydrocarbon group of 1 to 6 carbon atoms as described above, for example a methyl group, such a glycol mono-ether being methyl ethylene glycol. In general, however, the glycols themselves are preferred. Examples of such glycols are the simple dihydroxy alkanes such as ethylene glycol as well as those more complex compounds comprising two hydroxy groups attached to a chain containing both carbon and oxygen atoms, such as triethylene glycol, tetraethylene glycol and polyethylene glycol, for example of 4,000 daltons molecular weight. Triethylene glycol and especially tetraethylene glycol are of particular interest in view of their very low toxicity. By using such glycols and glycol ethers it is possible to increase solubility for many complexes to 10 to 20 mg/ml.

In the case of animals, compositions for parenteral administration are of greater interest than with humans. The problems of iron deficiency anaemia in newly born pigs arise primarily during the first three weeks or so of their life when a very rapid weight gain takes place. The usual routes for administration of the iron complexes of the present invention to young piglets are parenteral, for example intramuscular, or oral, for example as a liquid preparation "injected" into the mouth. However, an alternative approach is to enhance the iron content of the milk on which the piglets are feeding by treating the mother pig using oral or parenteral administration, for example with an injectable slow release preparation (such an approach may also be an interest in a human context). When it is applicable to feed piglets on foodstuffs other than the milk of the mother pig, it may also be possible to effect the pharmaceutical administration of the iron complex in this other foodstuff.

Other forms of administration than by injection or through the oral route may also be considered in both human and veterinary contexts, for example the use of suppositories for human administration.

Compositions may be formulated in unit dosage form, i.e. in the form of discrete portions containing a unit dose, or a multiple or sub-unit of a unit dose. Whilst the dosage of hydroxypyridone iron complex given will depend on various factors, including the particular compound which is employed in the composition, it may be stated by way of guidance that maintenance of the amount of iron present in the human body at a satisfactory level will often be achieved using a daily dosage, in terms of the iron content of the compound, which lies in a range from about 0.1 to 100 mg and often in a range from 0.5 to 10 mg, for example 1 or 2 mg, veterinary doses being on a similar g/Kg body weight ratio. However, it will be appreciated that it may be appropriate under certain circumstances to give daily dosages either below or above these levels. In general, the aim should be to provide the amount of iron required by the patient without administering any undue excess and the properties of the pharmaceutical compositions according to the present invention are particularly suited to the achievement of this aim.

Where desired, an iron complex of more than one hydroxypyridone as described above may be present in the pharmaceutical composition or indeed other active compounds may be included in the composition, for example compounds having the ability to facilitate the treatment of anaemia, such as folic acid. Another additional component which may be included in the composition, if desired, is a source of zinc. Iron compounds used in the treatment of iron deficiency anaemia can inhibit the mechanism of zinc uptake in the body and this can cause serious side effects in the foetus when treating anaemia in a pregnant female. It is believed, however, that the iron complexes of the present invention have a further advantage in that they either do not have this effect or exhibit the effect at a lower level than the compounds at present used in the treatment of anaemia. Accordingly, it may often be the case that the level of zinc providing compound added to the composition may not require to be high or, with preferred formulations of the iron complexes, may be dispensed with altogether.

It has never before been appreciated that the iron complexes such as those described herein might be used, and with great advantage, in a pharmaceutical context. Accordingly the present invention includes an iron complex of a 3-hydroxypyrid-2-one or 3-hydroxypyrid-4-one as defined hereinbefore for use in medicine, particularly in the treatment of iron anaemia deficiency.

We have found that the iron complexes described herein are particularly suited to the treatment of iron anaemia deficiency both in humans and also in a veterinary context, particularly for the treatment of various mammalian species and especially pigs. The complexes will partition into n-octanol indicating that they are able to permeate biological membranes, this property being confirmed in practice by tests of the ability of the $^{59}$Fe labelled iron complexes to permeate erythrocytes. The ability of the compounds in this respect will depend on the nature of the N- or N- and C-substituents present therein and the reflection of this ability in the $K_{part}$ values of various compounds has been referred to hereinbefore.

The ability of the iron complexes of the present invention to promote iron uptake with a high level of efficiency, as compared with a range of other iron complexes currently marketed for the treatment of iron deficiency anaemia, has been confirmed by measurements in the rat small intestine. Once present in the bloodstream, the complexes will donate iron to transferrin, a position of equilibrium being set up between the complexes and transferrin. It is because of the existence of this equilibrium that the corresponding free hydroxypyridones may equally be used in the treatment of iron overload, although certain of these compounds may be of particular value for use in the free state for iron removal and others may be of particular value for use as iron complexes for iron supply. Preliminary experiments have suggested that the 3-hydroxypyrid-2-ones may be more efficient at donating iron to transferrin than the 3-hydroxypyrid-4-ones.

Certain aspects of their formulation may enhance the activity of the complexes in particular contexts. Thus, although the neutral 3:1 ferric complexes are of particular value as being stable over a wide pH range from about 4 or 5 up to 10, they will dissociate at the pH values of less than 4 prevailing in the stomach to form a mixture of the 2:1 and 1:1 complex together with the free hydroxypyridone. Firstly, one of several variations may be employed which avoid or reduce exposure of the iron complex to the acidic conditions of the stomach. Such approaches may involve various types of controlled release system, ranging from one, which may for example be based on a polymer, which simply provides a delayed release of the complex with time, through a system which is resistant to dissociation under acidic conditions, for example by the use of buffering, to a system which is biased towards release under conditions such as prevail in the small intestine, for example a pH sensitive system which is stabilised towards a pH of 1 to 3 such as prevails in the stomach but not one of 7 to 9 such as prevails in the small intestine. Since the pH of the stomach is higher after a meal, it may be advantageous, whatever method of formulation is used, to administer the iron complexes at such a time.

A particularly convenient approach to a controlled release composition involves encapsulating the iron complex by a material which is resistant to dissociation in the stomach but which is adapted towards dissociation in the small intestine (or possibly, if the dissociation is slow, in the large intestine). Such encapsulation may be achieved with liposomes, phospholipids generally being resistant to dissociation under acidic conditions. The liposomally entrapped 3:1 iron(III) complexes can therefore survive the acid environment of the stomach without dissociating to the 2:1 and 1:1 complexes, and the free hydroxypyrone. On entry into the small intestine, the pancreatic enzymes rapidly destroy the phospholipid-dependent structure of the liposomes thereby releasing the 3:1 complex. Liposome disruption is further facilitated by the presence of bile salts. However, it is usually it is more convenient to effect the encapsulation, including micro-encapsulation, by the use of a solid composition of a pH sensitive nature.

The preparation of solid compositions adapted to resist dissociation under acidic conditions but adapted towards dissociation under non-acidic conditions is well known in the art and most often involves the use of enteric coating, whereby tablets, capsules, etc, or the inidividual particles or granules contained therein, are coated with a suitable material. Such procedures are described, for example, in the article entitled "Production of enteric coated capsules" by Jones in Manufacturing Chemist and Aerosol News, May 1970, and in such standard reference books as "Pharmaceutical Dosage Forms, Volume III by Liebermann and Lackmann (published by Marcel Decker). One particular method of encapsulation involves the use of gelatine capsules coated with a cellulose acetate phthalate/diethylphthalate layer. This coating protects the gelatin capsule from the action of water under the acid conditions of the stomach where the coating is protonated and therefore stable. The coating is however destabilised under the neutral/alkaline conditions of the intestine where it is not protonated, thereby allowing water to act on the gelatin. Once released in the intestine the rate of permeation of the intestine wall by the water soluble 3:1 iron-(III) complex is relatively constant irrespective of the position within the intestine, i.e. whether in the jejunum, ileum or large intestine. Other examples of methods of formulation which may be used include the use of polymeric hydrogel formulations which do not actually encapsulate the iron complex but which are resistant to dissociation under acidic conditions.

A second approach to countering the effect of the acidic conditions prevailing in the stomach is to formulate the iron complex in the pharmaceutical composition together with the metal-free hydroxypyridone from which it is derived. The dissociation of the neutral 3:1 ferric complex, for example, involves various equilibria between this complex, the 2:1 and 1:1 complexes, and the metal-free compound, so that the presence of the latter will inhibit this dissociation. Any proportion of the free compound can be advantageous in this context but little further advantage accrues from increasing the proportion beyond a certain level. A preferred range for the molar proportion of the free compound present in compositions according to the present invention is thus from 0 to 20 moles free hydroxypyridone:1 mole of iron complex, particularly the neutral 3:1 iron-(III) complex. Conveniently, a proportion of up to no more than 5 or 10 moles:1 mole is used with a lower level of 1 or 2 moles:1 mole, although to obtain a marked effect upon dissociation of the iron complex a proportion of at least 5 or 10 moles:1 mole is usually employed. Thus, a preferred range is from 3 moles:1 to 10 moles:1 mole. The use of such a mixture is an important feature of the present invention since it can enable one to obtain almost quantitative uptake of iron from the complex. It should be appreciated, however, that the equilibrium between the complexes of various types and the metal-free compound will be effected by any take up of the latter in the body and the degree of such uptake from the stomach, for example, will depend on the particular metal-free compound. The nature of the N-substituent, for example, may therefore have a marked effect on the behaviour of the complex/metal-free compound system, and in selecting such N-substituents this fact should be taken into account.

A further advantage than prevention of dissociation of the iron complex under acidic conditions may accrue from the use of a free hydroxypyridone in admixture with its iron complex. Thus, in certain pathological conditions there may be an excess of iron deposited at certain sites even though the patient exhibits an overall anaemia. In patients having such conditions the use of such a mixture has the advantage that the iron complex will remedy the overall anaemia whilst the free hydroxypyridone will act to remove iron from pathological to physiological sites. Moreover, there may be an advantage in formulating the iron complex of one hydroxypyridone as described herein with another one of such hydroxypyridones in free form (the same group of hydroxypyridones in metal-free form are the subject of our further application of even date herewith) or with a mixture of the corresponding free hydroxypyridone, present primarily to prevent dissociation of the iron complex, and of another such hydroxypyridone in free form, present primarily to effect iron transfer. Thus, it is preferable for the hydroxypyridone present in an iron donor to be rapidly metabolized so as to effect its removal from the system once it has given up its iron at an appropriate site in the system, whilst it is preferable for a hydroxypyridone being used as an iron remover not to be rapidly metabolized so that it remains in the system, taking up iron, for an extended period. For this reason the use of different hydroxypyridones in the free form and as the iron complex has certain advantages. Moreover, different hydroxypyridones may, for other reasons, function more efficiently either in the free form as an iron remover or in complex form as an iron donor. Of some especial interest are mixtures of an iron complex of a hydroxypyrid-2-one with a free hydroxypyrid-4-one, and optionally also with the corresponding free hydroxypyrid-2-one. If desired, the free hydroxypyridone may alternatively be used in the form of a salt formed at the hydroxy group thereof through its conversion to the anion (OH→O$^-$) and containing a physiologically acceptable cation, for example as described hereinbefore.

It will be appreciated that, as an alternative to combination with a different free hydroxypyridone of the same type, the iron complex may be used in combination with another iron chelating agent. In particular, this iron chelating agent may be one such as is described in UK patent application No. 8308056, published as GB No. 2,118,176A (U.S. application Ser. No. 478,493), being a 3-hydroxypyrid-2-one or 3-hydroxypyrid-4-one in which the hydrogen atom attached to the nitrogen atom is replaced by an aliphatic hydrocarbon group and, optionally, in which a hydrogen atom attached to one or more ring carbon atoms is also replaced by an aliphatic hydrocarbon group, or a salt thereof containing a physiologically acceptable cation. Other types of free hydroxypyridone with which the iron complex may be combined are described in UK patent application No. 8325496 published as Application No. GB 2,146,990A (U.S. application Ser. No. 651,772), now U.S. Pat. No. 4,587,240.

The present invention thus includes a mixture of an iron complex of a 3-hydroxypyrid-2-one or 3-hydroxypyrid-4-one in which the hydrogen atom attached to the nitrogen atom is replaced by an aliphatic acyl group, by an aliphatic hydrocarbon group, or by an aliphatic hydrocarbon group substituted by one, or except in the case of ionisable groups, more than one substituent selected from aliphatic acyl, alkoxy, aliphatic amine, aliphatic amide, carboxy, aliphatic ester, halogen, hydroxy and sulpho groups and, optionally, in which one or more of the hydrogen atoms attached to ring carbon atoms are replaced by one of said substituents, by an aliphatic hydrocarbon group, or by an aliphatic hydrocarbon group substitued by an alkoxy, aliphatic ester, halogen or hydroxy group, but excluding compounds in which said replacement of hydrogen atoms is effected only by aliphatic hydrocarbon groups, together with a different 3-hydroxypyrid-2-one or 3-hydroxypyrid-4-one in which the hydrogen atom attached to the nitrogen atom is replaced by an aliphatic acyl group, by an aliphatic hydrocarbon group, or by an aliphatic hydrocarbon group substituted by one, or except in the case of ionisable groups, more than one substituent selected from aliphatic acyl, alkoxy, aliphatic amine, aliphatic amide, carboxy, aliphatic ester, halogen, hydroxy and sulpho groups and, optionally, in which one or more of the hydrogen atoms attached to ring carbon atoms are replaced by one of said substituents, by an aliphatic hydrocarbon group, or by an aliphatic hydrocarbon group substituted by an alkoxy, aliphatic ester, halogen or hydroxy group, or a salt of such a different pyridone containing a physiologically acceptable ion or ions.

When a metal-free 3-hydroxypyrid-2-one or 3-hydroxypyrid-4-one is present in admixture with the iron complex of a 3-hydroxypyrid-4-one or 3-hydroxypyrid-2-one for the purpose of acting as an iron remover, then the amount of the former may be different than when the free hydroxypyridone necessarily corresponds to that present in the iron complex and is present primarily to prevent dissociation. Thus the daily dosage of the iron complex may be as above and the daily dosage of the free hydroxypyridone may be that quoted in our co-pending application of even date herewith, Ser. No. 478,493, and in UK patent application GB No. 2,118,176A. i.e. about 0.1 g to 5 g for human use, particularly 0.5 g to 2 g, from which it will be seen that the proportion of iron complex and free hydroxypyridone used in such a context may extend across a wide range but preferred amounts of the free compound tend to be higher than in the other instance.

It will be appreciated that the present invention also includes a method for the treatment of a patient which comprises administering to said patient an amount of an iron complex of a 3-hydroxypyrid-2-one or 3-hydroxypyrid-4-one as described hereinbefore in order to effect an increase in the levels of iron in the patient's blood stream.

In addition to the pharmaceutical uses of the iron complexes discussed above they are also of potential interest as a source of iron in various other contexts including in cell and bacterial growth, in plant growth, as a colouring agent and in the control of iron transport across membranes.

This invention is illustrated by the following Examples.

EXAMPLES

EXAMPLE 1

Preparation of the Iron Complexes

The iron complex of 3-hydroxy-1-(2'-hydroxyethyl)-2-methylpyrid-4-one is prepared by either procedure (a) or procedure (b).

(a) An aqueous solution of ferric chloride is reacted for 5 minutes at room temperature with an aqueous solution containing 3 molar equivalents of 3-hydroxy-1-(2'-hydroxyethyl)-2-methylpyrid-4-one. The resultant solution is adjusted to pH 7.0 using 2 molar aqueous sodium hydroxide and is then freeze dried. The resulting powder is extracted with chloroform, filtered and the filtrate subjected to rotary evaporation to give an essentially quantitative yield of the neutral complex containing the 3-hydroxy-1-(2'-hydroxyethyl)-2-methylpyrid-4-one anion and the ferric cation in 3:1 proportion. Recrystallisation of the 3:1 complex from ethanol gives wine coloured crystals, m.p. 330°–340° C., $\nu_{max}$ (nujol) 1,600, 1,500 cm$^{-1}$.

(b) An ethanolic solution of ferric chloride is reacted for 5 minutes at room temperature with a chloroform solution containing 3 molar equivalents of 3-hydroxy-1-(2'-hydroxyethyl)-2-methylpyrid-4-one. The resultant solution is neutralised by the addition of solid sodium carbonate, the precipitated sodium chloride removed by filtration and the filtrate evaporated to give an essentially quantitative yield of the 3:1 complex, m.p. 330°–340° C.

The 3:1 iron(III) complex of 1-(2'-carboxyethyl)-3-hydroxy-2-methylpyrid-4-one is prepared by a procedure analogous to (a) above and has m.p.>300° C., $\nu_{max}$ (nujol) 1500, 1550, 1590 cm$^{-1}$. The 3:1 iron(III) complexes of 3-hydroxy-1-methyoxycarbonylmethylpyrid-2-one and of 3-hydroxy-1-(N-propylcarbamoylmethyl)-pyrid-2-one are prepared by a procedure analogous to (b) above and have, respectively, m.p. 305°–310° C. decomp., $\nu_{max}$ (nujol) 1540, 1630, 1750 cm$^{-1}$.

When an excess (5 to 50 molar equivalents) of any pyridone is used, both procedure (a) and procedure (b) lead to an essentially quantitative yield of the excess pyridone in free form in admixture with the 3:1 complex.

The partition coefficient $K_{part}$, being the ratio (concentration of compound in n-octanol)/(concentration of compound in aqueous phase) on partition between n-octanol and aqueous tris hydrochloride (20 mM, pH 7.4; tris represents 2-amino-2-hydroxymethylpropane 1,3-diol), is measured at 20° C. for the 3:1 iron(III) complexes of each of the compounds listed in Table 1 and also for the iron-free compound (at $10^{-4}$M) by spectrophotometry. The solutions of the complexes are either produced by dissolving the pre-formed complex in the aqueous tris hydrochloride or are prepared in situ in the buffer by the admixture of a 3:1 molar ratio of the pyridone and ferric chloride, the pH thereafter being readjusted to 7.4 if necessary (the same product will be obtained in the buffer solution irrespective of whether the pyridone used is in a salt form or not). Acid washed glassware is used throughout and, following mixing of 5 ml of the $10^{-4}$M aqueous solution with 5 ml of n-octanol for 1 minute, the aqueous n-octanol mixture is centrifuged at 1,000 g for 30 seconds. The two resulting phases are separated for a concentration determination by spectrophotometry on each. For the free hydroxypyridones, the range 220–340 nm is used for concentration determinations whilst for the iron complexes the range 340–640 nm is used. Values typical of those obtained are shown in Table 1.

TABLE 1

| | Partition coefficients | |
|---|---|---|
| Compound | Free compound | Iron complex [$Fe^{III}$-(compound)$_3$] |
| 1-acetyl-3-hydroxypyrid-2-one | 0.55 | 0.24 |
| 1-ethoxycarbonylmethyl-3-hydroxypyrid-2-one | 0.5 | 0.19 |
| 3-hydroxy-1-methoxycarbonylmethylpyrid-2-one | 0.2 | 0.02 |
| 1-(N—ethylcarbamoylmethyl-3-hydroxypyrid-2-one | 0.12 | 0.01 |
| 3-hydroxy-1-(N—methylcarbamoylmethyl)-pyrid-2-one | 0.06 | 0.005 |
| 3-hydroxy-1-(N—propylcarbamoylmethyl)-pyrid-2-one | 0.35 | 0.14 |
| 3-hydroxy-1-[N—(2'-methylethyl)-carbamoylmethyl]-pyrid-2-one | 0.34 | 0.15 |
| 1-(N—butylcarbamoylmethyl)-3-hydroxypyrid-2-one | 1.89 | 5.12 |
| 3-hydroxy-1-(2'-hydroxyethyl)-2-methylpyrid-4-one | <0.002 | <0.002 |
| 3-hydroxy-1-(3'-hydroxypropyl)-2-methylpyrid-4-one | 0.10 | 0.06 |
| 3-hydroxy-1-(4-hydroxybutyl)-2-methylpyrid-4-one | 0.14 | 0.03 |
| 3-hydroxy-1-(5'-hydroxypentyl-2-methylpyrid-4-one | 0.28 | 0.04 |
| 1-(5'-acetoxypentyl-3-hydroxy-2-methylpyrid-4-one | 0.45 | 0.03 |
| 1-carboxymethyl-3-hydroxy-2-methylpyrid-4-one | <0.002 | <0.002 |
| 1-(2'-carboxyethyl)-3-hydroxy-2-methylpyrid-4-one | 0.45 | 0.03 |
| 1-(2'-aminoethyl)-3-hydroxy-2-methylpyrid-4-one | <0.002 | <0.002 |
| 3-hydroxy-6-hydroxymethyl-1-methylpyrid-4-one | 0.03 | 0.01 |
| 1-ethyl-3-hydroxy-6-hydroxymethyl pyrid-4-one | 0.06 | 0.07 |

The ability of the complexes of 1-acetyl-3-hydroxypyrid-2-one and 1-ethyl-3-hydroxy-6-hydroxymethylpyrid-4-one to bind to haemoglobin is investigated by studying the elution profile of a $^{59}$Fe label when a mixture of haemoglobin and the $^{59}$Fe-labelled 3:1 (pyridone:iron) neutral complex (at 1 mM concentration) is applied to a PD-10 column (Sephadex G-10 gel permeation column - Pharmacia). The two complexes advantageously show no detectable haemoglobin binding ability.

PREPARATION OF HYDROXYPYRIDONE STARTING MATERIALS

Various hydroxypyridones for the preparation of the iron complexes of Table 1 and of other iron complexes according to the present invention are obtained as follows.

(A) The preparation of 1-acetyl-3-hydroxypyrid-2-one 2,3-Dihydroxypyridine (5.55 g) is refluxed with acetylbromide (10 ml) overnight. The reaction mixture is allowed to cool and water (10 ml) is added. The resulting suspension is extracted with methylene chloride and the methylene chloride solution is dried over $Na_2SO_4$ and evaporated. The resultant residue is recrystallised from petroleum ether (80°–100° C.) to give 1-acetyl-3-hydroxypyrid-2-one as white crystals (2.8 g), m.p. 140°–141° C.; $v_{max}$ (nujol) 1680, 3120 cm$^{-1}$; $\delta$(d$_6$DMSO), 2.2 (s, 3H), 6.1 (t, 1H), 6.65 (m, 1H), 7.2 (d, 1H).

(B) The preparation of 1-ethoxycarbonylmethyl-3-hydroxy pyrid-2-one 2,3-Dihydroxypyridine (5 g) is suspended in ethylbromoacetate (20 ml) and the mixture heated in a sealed tube for 24 hours at 140° C. The tube is then cooled in solid $CO_2$ and opened. The contents are subjected to rotary evaporation at 50° C. to yield a yellow solid. Recrystallisation of this solid from water yields 1-ethoxycarbonylmethyl-3-hydroxypyrid-2-one as white crystals (5.4 g), m.p. 141°–151° C.; $v_{max}$ (nujol) 1645, 1720 cm$^{-1}$; $\delta$(d$_6$DMSO), 1.0 (t, 3H), 4.0 (q, 2H), 4.55 (s, 2H), 5.95 (t, 1H), 6.6 (d, 1H), 7.05 (d, 1H).

(C) The preparation of 1-carboxymethyl-3-hydroxypyrid-2-one

1-Ethoxycarbonylmethyl-3-hydroxypyrid-2-one (2 g) is dissolved in 15 ml of 1:2 v/v ethanol/water containing sufficient ammonium hydroxide to create a pH of 12.0. The solution is heated at 60° C. for 30 minutes, cooled, and acidified to pH 3.0 by the addition of formic acid. The solution is rotary evaporated to remove most of the ethanol and then freeze dried for 20 hours to remove the water, formic acid and ammonium formate. The resulting solid is recrystallised from water to yield white crystals (1.4 g), m.p. 203°–205° C.; $v_{max}$ (nujol) 1540, 1590, 1640, 1695, 3240 cm$^{-1}$; $\delta$(d$_6$DMSO) 4.5 (s, 2H), 5.95 (t, 1H), 6.6 (d, 1H), 7.0 (d, 1H).

(D) The preparation of 3-hydroxy-1-methoxycarbonylmethylpyrid-2-one

1-Carboxymethyl-3-hydroxypyrid-2-one (1 g), prepared as described under (C), is refluxed in methanolic hydrochloric acid for 2 hours. The solvent is removed by rotary evaporation and the residue recrystallised from water to give 3-hydroxy-1-methoxycarbonylmethylpyrid-2-one in 60% yield, m.p. 141°–142° C.; $v_{max}$ (nujol) 1560, 1595, 1645, 1730, 3220 cm$^{-1}$; $\delta$(d$^6$DMSO) 3.55 (s, 3H), 4.65 (s, 2H), 6.05 (t, 1H), 6.7 (d, 1H), 7.1 (d, 1H) 9.2 (s, 1H).

The Preparation of 1-(N-ethylcarbamoylmethyl)-3-hydroxypyrid-2-one

3-Benzyloxy-1-carboxymethylpyrid-2-one

1-Ethoxycarbonylmethyl-3-hydroxypyrid-2-one (10 g), prepared as described under (B), is dissolved in methanol/water (9:1 v/v) (400 ml). To this solution is added benzyl chloride (3 molar excess) and NaOH until the pH is above 12. The mixture is then refluxed for six hours to give a clear orange solution. The methanol is removed by rotary evaporation and the aqueous solution is extracted with dichloromethane to remove excess benzyl chloride. The aqueous phase is diluted slightly by adding extra water and then acidified to pH 2 using concentrated hydrochloric acid which results in the precipitation of a beige solid. The mixture is cooled and the precipitate filtered off and washed with diethyl ether. The crude product is recrystallised from ethanol to give 3-benzyloxy-1-carboxymethylpyrid-2-one (5.4 g, 41%), m.p. 176°–177° C.

3-Benzyloxy-1-(succinimido-oxycarbonylmethyl)-pyrid-2-one

3-Benzyloxy-1-carboxymethylpyrid-2-one (2 g) is dissolved in dimethylformamide (DMF) (25 ml) and to this solution is added N-hydroxysuccinimide (1 g). The resultant solution is cooled and to it is added dicyclohexylcarbodiimide (DCCI) (11.8 g) in DMF (5 ml). The mixture is allowed to stand overnight to give a brown supernatant and a white precipitate. The precipitate is filtered off, washed with a little DMF and then evaporated to dryness under high vacuum. The crude product is dissolved in a minimum volume of dichloromethane and diethyl ether is added to this solution until it becomes cloudy. The solution is then cooled and the resultant precipitate is filtered off and washed with a little diethyl ether to give 3-benzyloxy-1-(succinimidooxycarbonylmethyl)-pyrid-2-one (2.26 g, 82%), m.p. 187°–188° C.

3-Benzyloxy-1-(N-ethylcarbamoylmethyl)-pyrid-2-one

3-Benzyloxy-1-(succinimido-oxycarbonylmethyl)-pyrid-2-one (1 g) is dissolved in dichloromethane (100 ml) and to this solution is added ethylamine in a 2 molar excess. The mixture is allowed to stand for five minutes and then the N-hydroxysuccinimide liberated by the reaction is extracted with 1M sodium bicarbonate (2×25 ml). The organic layer is dried over anhydrous sodium sulphate, filtered, and evaporated to give 3-benxyloxy-1(N-ethylcarbamoylmethyl)-pyrid-2-one as a grey solid in 50% yield, m.p. 171°–172° C.

1-(N-ethylcarbamoylmethyl)-3-hydroxypyrid-2-one

3-Benzyloxyl-(N-ethylcarbamoylmethyl)-pyrid-2-one (1 g) is dissolved in 50:50 v/v aqueous ethanol. Platinum/carbon catalyst (100 mg) is added and the solution is hydrogenated at 20° C. and atmospheric pressure for eight hours. The mixture is filtered, the filtrate subjected to rotary evaporation and the resulting residue recrystallised from ethanol to give 1-(N-ethylcarbamoylmethyl)-3-hydroxypyrid-2-one in 70% yield, m.p. 214°–215° C., $\nu_{max}$ (nujol) 1555, 1580, 1645, 1675, 3260, 3400 cm$^{-1}$, $\delta$(d$_6$DMSO) 1.0 (t, 3H), 3.05 (m, 2H), 4.5 (s,2H), 6.05 (t, 1H), 6.7 (d, 1H), 7.05 (d, 1H), 8.2,(s, 1H).

(F) The preparation of 3-hydroxy-1-(N-methylcarbamoylmethyl)pyrid-2-one

3-Benzyloxy-1-(succinimido-oxycarbonylmethyl)-pyrid-2-one (1 g), prepared as described under (E), is reacted with methylamine under substantially similar conditions to those described under (E) for the reaction of this compound with ethylamine to give 3-benzyloxy-1-(N-methylcarbamoylmethyl)-pyrid-2-one as a white solid in 84% yield, m.p.=182°–183° C.

This compound is hydrogenated as described under (E) for the corresponding ethyl analogue to give 3-hydroxy-(N-methylcarbamoylmethyl)-pyrid-2-one in 60% yield, m.p.=204°–205° C.; $\nu_{max}$ (nujol) 1560, 1585, 1645, 1685, 2950, 3275 cm$^-$. $\delta$(d6DMSO) 2.40, 2.46 (2 x s, 3H), 4.35 (s, 2H), 6.55 (d, 1H), 6.95 (d, 1H), 7.95 (s, 1H).

(G) The preparation of 3-hydroxy-1-(N-propylcarbamoylmethyl)pyrid-2-one

3-Benzyloxy-1-(succinimido-oxycarbonylmethyl)-pyrid-2-one (1 g), prepared as described under (E), is reacted with n-propylamine under substantially similar conditions to those described under (E) for the reaction of this compound with ethylamine to give 3-benzyloxy-1-(N-propylcarbamoylmethyl)-pyrid-2-one as a beige solid in 60% yield, m.p. 156°–157° C. This compound is hydrogenated as described under (E) for the corresponding ethyl analogue to give 3-hydroxy-1-(N-propylcarbamoylmethyl)-pyrid-2-one in 47% yield, m.p. 204°–205° C.; $\nu_{max}$ (nujol) 1560, 1580, 1640, 3050, 3200 cm$^{-1}$, $\delta$(d$^6$DMSO) 0.85 (t, 3H), 1.5 (m, 2H), 3.0 (q, 3H), 4.5 (s, 2H), 6.05 (t, 1H) 6.7 (d, 1H), 7.05 (d, 1H), 8.1 (s, 1H), 8.95 (s, 1H).

(H) The preparation of 3-hydroxy-1-[N-(2'-methylethyl)carbamoylmethyl]-pyrid-2-one 3-Benzyloxy-1-(succinimido-oxycarbonylmethyl)-pyrid-2-one (1 g), prepared as described under (E), is reacted with isopropylamine under substantially similar conditions to those described under (E) for the reaction of this compound with ethylamine to give 3-benzyloxy-1-[N-(2'-methylethyl)-carbamoylmethyl]-pyrid-2-one. This compound is hydrogenated as described under (E) for the corresponding ethyl analogue to give 3-hydroxy-1-[N-(2'-methylethyl)-carbamoylmethyl]-pyrid-2-one as a silvery powder in 60% yield, m.p. 238°–241° C.; $\nu_{max}$ (nujol) 1570, 1595, 1650, 3270 cm$^{-1}$; $\delta$(d$_6$DMSO) 0.95 (d, 6H), 3.7 (m, 1H), 4.4 (s, 2H), 5.95 (t, 1H) 6.53 (d, 1H), 6.98 (d, 1H), 7.96 (d, 1H), 8.85 (s, 1H).

(I) The preparation of 1-(N-butylcarbamoylmethyl)-3-hydroxypyrid-2-one

3-Benzyloxy-1-(succinimido-oxycarbonylmethyl)-pyrid-2-one (1 g), prepared as described under (E), is reacted with n-butylamine under substantially similar conditions to those described under (E) for the reaction of this compound with ethylamine to give 3-benzyloxy-1-(N-butylcarbamoylmsthyl)-pyrid-2-one. This compound is hydrogenated as described under (E) for the corresponding ethyl analogue to give 1-(N-butylcarbamoylmethyl)-3-hydroxypyrid-2-one as colourless needles of m.p. 199°–200° C.; $\nu_{max}$ (nujol) 1565, 1595, 1650, 1680, 3100, 3270 cm$^{-1}$; $\delta$(d$_6$DMSO), 0.8 (t, 3H), 1.3 (m, 4H), 3.0 (d, 2H), 4.43 (s, 2H) 5.95 (t, 1H) 6.63 (d, 1H), 6.96 (d, 1H), 8.0 (t, 1H), 8.86 (s, 1H).

(J) The preparation of 1-acetyl-3-hydroxy-2-methylpyrid-4-one 3-Benzyloxy-2-methyl-4-pyrone 3-Hydroxy-2-methyl-4-pyrone (22.2 g) in methanol (225 ml) is added to aqueous sodium hydroxide (25 ml H$_2$O containing 7.5 g NaOH). Benzyl chloride (25.5 g) is added and the mixture is refluxed for 6 hours and is then allowed to cool overnight. The bulk of the methanol is removed under vacuum and the residue is treated with water (50 ml). The mixture is extracted into dichloromethane (3×25 ml). The extracts are combined, washed with 5% w/v NaOH (2×25 ml), then water (2×25 ml) and dried over magnesium sulphate. Evaporation of the solvent gives crude 3-benzyloxy-2-methyl- 4-pyrone (35 g, 92%) which is purified by distillation in nitrogen under reduced pressure to yield a colourless oil (28 g) of b.p. 148° C./0.2 mm.

3-Benzyloxy-2-methylpyrid-4-one

3-Benzyloxy-2-methyl-4-pyrone (20 g), concentrated (s.g. 0.880) ammonia (200 ml) and ethanol (100 ml) are mixed and kept at room temperature for 3 days. The solvent and excess ammonia are then removed by rotary evaporation to yield an oil which on trituration with acetone gives 3-benzyloxy-2-methylpyrid-4-one as white crystals m.p. 162°–163° C.

1-Acetyl-3-benyloxy-2-methylpyrid-4-one

3-Benzyloxy-2-methylpyrid-4-one (4 g) is dissolved in dry acetone (100 ml). Acetylbromide (3 g) and triethylamine (2.7 g) are added and the resulting mixture is mechanically stirred overnight. The mixture is then filtered and the filtrate is rotary evaporated to dryness. The residue is dissolved in methylene chloride and washed with dilute hydrochloric acid (pH 3.0), then twice with water, and is dried over $Na_2SO_4$ and rotary evaporated to yield a solid residue. Recrystallisation of this residue from an ethylacetate/hexane mixture gives 1-acetyl-3-benzyloxy-2-methylpyrid-4-one as an oil (3.1 g).

1-Acetyl-3-hydroxy-2-methylpyrid-4-one

1-Acetyl-3-benzyloxy-2-methylpryid-4-one (2 g) is treated with 45% w/v HBr-acetic acid (10 ml) for 1 hour at 100° C. The solution is rotary evaporated to dryness at 70° C. and triturated with an ethyl acetate/methanol (20.1 v/v) mixture. On standing overnight at 4° C. pale brown crystals are deposited (1.2 g) and these are recrystallised from an ethyl acetate/methanol mixture to yield 1-acetyl-3-hydroxy-2-methylpyrid-4-one as white crystals, m.p. 152°–160° C.; $\delta_{max}$ (nujol) 1630, 1680 cm$^{-1}$; $\delta(d_6DMSO)$, 2.2 (s, 3H), 2.5 (s, 3H), 7.25 (d, 1H), 8.15 (d, 1H).

(K) The preparation of 3-hydroxy-1-(2'-hydroxyethyl)-2-methylpyrid-4-one

3-Benzyloxy-1-(2'-hydroxyethyl)-2-methylpyrid-4-one

3-Benzyloxy-2-methyl-4-pyrone (4.8 g), prepared as described under (J), and 2-hydroxyethylamine (1.22 g) are dissolved in water (220 ml) and ethanol (100 ml) containing sodium hydroxide (2 g) is added. The mixture is stirred at room temperature for 6 days and is then acidified with concentrated hydrochloric acid to pH 2, and evaporated to dryness. The resulting colourless solid is washed with water and extracted into chloroform (2×50 ml). The chloroform extracts are combined, dried over magnesium sulphate, and evaporated to yield 3-benzyloxy-1-(2'-hydroxyethyl)-2-methylpyrid-4-one, as a white solid (3.4 g), m.p. 198°–199° C.

3-Hydroxy-1-(2'-hydroxyethyl)-2-methylpyrid-4-one

3-Benzyloxy-1-(2'-hydroxyethyl)-2-methylpyrid-4-one (2 g) is added to concentrated hydrobromic acid (10 ml) and the mixture is heated on a steam bath for 30 minutes. The resultant product is then recrystallised from water to yield 3-hydroxy-1(2'-hydroxyethyl)-2-methylpyrid-4-one as white crystals (0.8 g), m.p. 164°–165° C.; $\delta_{max}$ (nujol) 1630, 3150, 3350 cm$^{-1}$; $\delta(d_b$ DMSO), 2.5 (s, 3H), 3.7 (t, 2H), 4.35 (t, 2H), 7.25 (3, 1H), 8.15 (d, 1H).

(L) The preparation of 3-hydroxy-1-(3'-hydroxypropyl)-2-methylpyrid-4-one

3-Benzyloxy-2-methyl-4-pyrone, prepared as described under (J), is reacted with 3-hydroxypropylamine under substantially similar conditions to those described under (K) for reaction with 2-hydroxyethylamine to give 3-benzyloxy-1-(3'-hydroxypropyl)-2-methylpyrid-4-one. This is deprotected using the procedure described under (K) to give 3-hydroxy-1-(3'-hydroxypropyl)-2-methylpyrid-4-one as white crystals, m.p. 111°–113° C.; $\delta_{max}$ (nujol) 1630, 3150, 3350 cm$^{-1}$, $\delta(d_6$ DMSO) 1.8 (m, 2H), 2.4 (s, 3H), 3.35 (t, 2H), 4.33 (t, 2H), 7.3 (d, 1H), 8.2 (d, 1H).

(M) The preparation of 3-hydroxy-1-(4'-hydroxybutyl)-2-methylpyrid-4-one

3-Benzyloxy-2-methyl-4-pyrone, prepared as described under (J), is reacted with 1-amino-4-hydroxybutane under substantially similar conditions to those described under (K) for reaction with 2-hydroxyethylamine to give 3-benzyloxy-1-(4'-hydroxybutyl)-2-methylpyrid-4-one. This is deprotected using the procedure described under (I) to give 3-hydroxy-1-(4'-hydroxybutyl)-2-methylpyrid-4-one as white crystals, m.p. 126°–128° C.; $\delta_{max}$ (nujol) 1630, 3350 cm$^{-1}$; $\delta(d_6DMSO)$ 1.5 (m, 4H), 2.45 (s, 3H), 3.35 (t, 2H), 4.30 (t, 2H), 7.25 (d 1H), 8.2 (d, 1H).

(N) The preparation of 3-hydroxy-1-(5'-hydroxypentyl)-2-methylpyrid-4-one

3-Benzyloxy-2-methyl-4-pyrone, prepared as described under (J), is reacted with 1-amino-5-hydroxypentane under substantially similar conditions to those described under (K) for reaction with 2-hydroxyethylamine to give 3-benzyloxy-1-(5'-hydroxypentyl)-2-methylpyrid-4-one. This is deprotected using the procedure described under (I) to give 3-hydroxy-1-(5'-hydroxypentyl)-2-methylpyrid-4-one as white crystals, m.p. 136°–138° C.; $\delta_{max}$ (nujol) 1625, 3350 cm$^{-1}$; $\delta(d_6DMSO)$ 1.3 (m, 6H), 2.40 (s, 3H), 3.25 (t, 2H), 4.20 (t, 2H), 7.20 (d, 1H), 8.15 (d, 1H).

(O) The preparation of 1-(5'-acetoxypentyl)-3-hydroxy-2-methylpyrid-4-one

3-Hydroxy-1-(5'-hydroxypentyl)-2-methylpyrid-4-one, prepared as described under (N), (2 g) is dissolved in glacial acetic acid containing about 1% w/v of hydrogen bromide and the solution is refluxed for 2 hours. The resultant mixture is subjected to rotary evaporation and the residue crystallised from aqueous ethonal to give 1-(5'-acetoxypentyl)-3-hydroxy-2-methylpyrid-4one in 65% yield, m.p. 132°–133° C., $\delta_{max}$ (nujol) 1520, 1540, 1580, 1635, 1735 cm$^{-1}$ and $\delta(d_6DMSO)$, 1.6 (m, 6H), 2.1 (s, 3H), 2.4 (s, 3H), 4.05 (m, 4H), 6.4 (d, 1H), 7.3 (d, 1H).

(P) The preparation of 1-carboxymethyl-3-hydroxy-2-methylpyrid-4-one

3-Benzyloxy-2-methyl-4-pyrone, prepared as described under (J), is reacted with glycine under substantially similar conditions to those described under (K) for reaction with 2-hydroxyethylamine to give 3-benzyloxy-1-carboxymethyl-3-hydroxy-2-methylpyrid-4-one, which is deprotected using the procedure described under (I) to give 1-carboxymethyl-3-hydroxy-2-methylpyrid-4-one as white crystals, m.p. >230° C.;

$\delta_{max}$ (nujol) 1625, 1645 cm$^{-1}$; $\delta$(d$_6$ DMSO) 1.9 (s, 3H), 4.3 (s. 2H), 5.9 (d, 1H), 7.35 (d, 1H).

(Q) The preparation of 1-(2'-carboxyethyl)-3-hydroxy-2-methylpyrid-4-one hydrochloride 3-Benzyloxy-1-(2'-carboxyethyl)-2-methylpyrid-4-one 3-Benzyloxy-2-methyl-4-pyrone, prepared as described under (J), (20 g) and beta-alanine (9 g) are dissolved in 3:2 v/v water/ethanol (500 ml) containing NaOH (10 g) to provide a solution with a pH of at least 13. The solution is refluxed for 15 minutes whereupon it turns from a light orange to an intense red colour. The solution is acidified to pH 7.0 and the ethanol is removed by rotary evaporation. The resulting aqueous solution is washed twice with ethylacetate (100 ml). This solution is then subjected to rotary evaporation until the volume is reduced to 100 ml and this reduced volume of solution is acidified to pH 3.0 to give a white precipitate, which is filtered off to give 3-benzyloxy-1-(2'-carboxyethyl)-2-methylpyrid-4-one in 70% yield, m.p. 156°–157° C. 1-(2'-Carboxyethyl)-3-hydroxy-2-methylpyrid-4-one hydrochloride 3-Benzyloxy-1-(2'-carboxyethyl-2-methylpyrid-4-one is subjected to hydrogenation in aqueous ethanol (1:1 v/v) in the presence of platinum/carbon catalyst (100 mg per gram of pyridone) for 8 hours at 20° C. and atmospheric pressure. Filtration, followed by rotary evaporation of the filtrate, yields a white solid which on recrystallisation from acetone and diethylether gives 1-(2'-carboxyethyl)-3-hydroxy-2-methylpyrid-4-one hydrochloride in 55% yield, m.p. <40° C.: $\delta_{max}$ (nujol) 1590, 1620, 1720 cm$^{-1}$ $\delta$(d$_6$DMSO) 2.5 (s, 3H), 2.8 (t, 2H), 4.45 (t, 2H), 7.35 (d, 1H), 8.2 (d, 1H).

(R) The preparation of 1-(2'-ethoxycarbonylethyl)-3-hydroxy-2-methylpyrid-4-one 1-(2'-Carboxyethyl)-3-hydroxy-2-methylpyrid-4-one hydrochloride (2 g), prepared as decribed under (Q), is dissolved in ethanol saturated with hydrogen chloride and the solution is refluxed for 3 hours. Rotary evaporation of the solution yields a white solid which on recrystallisation from ethanol gives 1-(2'-ethoxycarbonylethyl)-3-hydroxy-2-methylpyrid-2-one hydrochloride in 75% yield, m.p. 127°–130° C.; $\delta_{max}$ (nujol) 1530, 1620, 1720 cm$^{-1}$; $\delta$(d$_6$DMSO) 1.1 (t, 3H), 2.5 (s, 3H), 2.9 (t, 2H), 4.0 (q, 2H), 4.5 (t, 2H), 7.4 (d, 1H), 8.2 (d, 1H).

(S) The preparation of 3-hydroxy-1-(2'-methoxycarbonylethyl)-2-methylpyrid-4-one 1-(2'-carboxyethyl)-3-hydroxy-2-methylpyrid-4-one hydrochloride (2 g) prepared as described under (Q), is dissolved in methanol saturated with hydrogen chloride and the solution is refluxed for 3 hours. Rotary evaporation of the solution yields a white solid which on recrystallisation from methanol gives 3-hydroxy-1-(2'-methoxycarbonylethyl)-2-methylpyrid-4-one hydrochloride in 80% yield m.p. 140°–141° C., $\delta_{max}$ 1545, 1595, 1645, 1730, 1750 cm$^{-1}$, $\delta$(d$_6$DMSO), 2.45 (s, 3H), 2.85 (t, 2H), 3.5 (s, 3H), 4.45 (t, 2H), 7.30 (d, 1H), 8.15 (d, 1H).

(T) The preparation of 3-hydroxy-1-[2'-(N-propylcarbamoyl)ethyl]-2-methylpyrid-4-one 3-Benzyloxy-1-[2'-(succinimido-oxycarbonyl)-ethyl]-2-methylpyrid-4-one 3-Benzyloxy-1-(2'-carboxyethyl)-2-methylpyrid-2-one, prepared as described under (Q), (2.2 g) is dissolved in DMF (25 ml) and to the solution is added N-hydroxysuccinimide (1 g). This solution is cooled and to it is added dicyclohexylcarbodiimide (1.8 g) in DMF (5 ml). The mixture is allowed to stand overnight giving a dark coloured solution and white precipitate. The precipitate is removed by filtration and washed with DMF (3 ml). The solution is rotary evaporated to dryness and triturated with diethylether to give 3-benzyloxy-1-[2'-(succinimido-oxycarbonyl)-ethyl]-2-methylpyrid-4-one hydrochloride as a white solid in 55% yield, m.p. 45°–47° C.

3-Benzyloxy-1-[2'-(N-propylcarbamoyl)-ethyl]-2-methylpyrid-4-one

3-Benzyloxy-1-[2'-(succinimido-oxycarbonyl)-ethyl]-2-methylpyrid-2-one (1 g) is dissolved in chloroform (100 ml) and to this solution is added ethylamine in a 2 molar excess. The mixture is allowed to stand for 15 minutes and the N-hydroxysuccinimide liberated by the reaction is then extracted with 1M NaHCO$_3$ solution (2×25 ml). The organic layer is dried over Na$_2$SO$_4$, filtered and evaporated to dryness to give 3-benzyloxy-1-[2'-(N-propylcarbamoyl)-ethyl]-2-methylpyrid-4-one as a white solid in 40% yield, m.p. 146°–147° C.

3-Hydroxy-1-[2'-(N-propylcarboamoyl)-ethyl]-2methylpyrid-4-one

3-Benzyloxy-1-[2'-N-propylcarbamoyl)-ethyl]-2-methylpyrid4-one (5 g) is dissolved in 50:50 v/v aqueous ethanol. Platinum/carbon catalyst (100 mg) is added and the solution is hydrogenated at 20° C. and atmospheric pressure for 8 hours. The mixture is filtered, the filtrate subjected to rotary evaporation and the resulting residue recrystallised from ethanol to give 3-hydroxy-1-[2'-(N-propylcarbamoyl)-ethyl]-pyrid 4-one, m.p. 113°–114° C., $v_{max}$ (nujol) 1505, 1550, 1570, 1630, 1705, 3080, 3200 cm$^-$; $\delta$(d$_6$DMSO) 0.6 (t, 3H), 1.2 (sextuplet, 2H), 2.5 (s, 3H), 2.6, 2.8 (overlapping t and q, 4H), 4.5 (t, 2H), 7.2 (d, 1H), 8.1 (overlapping d and t, 2H).

(U) The preparation of 1-(2'-aminoethyl)-3-hydroxy-2-methylpyrid-4-one hydrochloride 3-Benzyloxy-2-methyl-4-pyrone, prepared as described under (D), (4 g) and ethylene diamine (1.5 g) are heated together under reflux in water (50 ml) and ethanol (17 ml) for 1 hour. The solvent is removed by rotary evaporation and the solid residue is heated at 80° C. with concentrated hydrochloric acid (50 ml) for 30 minutes. Excess acid is removed by rotary evaporation at 80° C. and the residue is slurried with acetone, yielding a pale brown solid (2.2 g). Recrystallisation from ethanol, containing a trace of hydrochloric acid yields 1-(2'-aminoethyl)-3-hydroxy-2-methylpyrid-4-one hydrochloride as white crystals, m.p. 280° C. (with decomposition); $v_{max}$ (nujol) 1620, 3150 cm$^{-1}$; $\delta$(D$_2$O) 2.5 (s, 3H), 3.5 (t, 2H) 4.5 (t, 2H), 7.1 (d, 1H), 8.1 (d, 1H).

(V) The preparation of 3-hydroxy-6-hydroxymethyl-1-methylpyrid-4-one

3-Benzyloxy-6-benzyloxymethylpyrid-4-one

Kojic acid (3-hydroxy-6-hydroxymethylpyrid-4-one) (11.5 g) in methanol (90 ml) is added to an aqueous solution of sodium hydroxide (3 g in 10 ml). Benzylchloride (10.2 g) is added and the mixture is stirred and refluxed for 6 hours. On cooling, crystals are obtained which are recrystallisated from methanol to give 3-benzyloxy-6-benzyloxymethylpyrid-4-one as white crystals (10 g), m.p. 103°–131° C.; $\delta(CDCl_3)$ 4.25 (s, 2H), 4.99 (s, 2H), 6.25 (s, 1H), 7.3 (s, 5H), 8.1 (s, 1H).

3-Hydroxy-6-hydroxymethyl-1-methylpyrid-4-one

3-Benzyloxy-6-benzyloxypyrid-4-one (5.0 g) and methylamine hydrochloride (1.56 g) are dissolved in aqueous ethanol (300 ml of 2:1 $H_2O$-$C_2H_5OH$ by volume containing 2 g of sodium hydroxide). The reaction mixture is stirred at room temperature for 6 days and then acidified with concentrated HCl to pH 2.0. The yellow mixture is evaporated to dryness and the resulting solid residue is heated under reflux with concentrated HCl (50 ml) for 30 minutes. The product is rotary evaporated to dryness yielding a brown residue which on trituration with acetone forms crystals. Recrystallisation of these from ethanol gives 3-hydroxymethyl-1-methylpyrid-4-one in 15% yield, m.p. 185°–186° C.; $\delta(d_6DMSO)$, 3.9 (s, 3H), 4.6 (s, 2H), 7.4 (s, 1H), 8.3 (s, 1H).

(W) The preparation of 1-ethyl-3-hydroxy-6-hydroxy-methylpyrid-4-one

3-Benzyloxy-6-benzyloxypyrid-4-one, prepared as described under (V), is reacted with ethylamine hydrochloride under substantially similar conditions to those described under (V) for reaction with methylamine hydrochloride to give 1-ethyl-3-hydroxy-6-hydroxymethylpyrid-4-one as white crystals, m.p. 143°–145° C.; $\delta(d_6DMSO)$ 1.1 (t, 3H), 4.0 (q, 2H), 4.3 (s, 2H), 7.2 (s, 1H), 8.1 (s, 1H).

(X) The preparation of 1-(2'-aminoethyl)-3-hydroxypyrid-4-one

3-Benzyloxy-4-pyrone is prepared from 3-hydroxy-4-pyrone as described by Spenser et al, Canadian Journal of Chemistry, 1962, 40, 1377 and has m.p. 82°–85° C. A mixture of this compound (1 g) and ethylenediamine (0.37 g) in water (12 ml) is heated under reflux for 1 hour. The reaction mixture is evaporated to dryness and the residue is treated with concentrated hydrochloric acid (12 ml) and the mixture is heated on a steam bath for 30 minutes. The excess acid and water are evaporated under reduced pressure to give a solid brown residue. This is slurried in acetone, then filtered off and recrystallised from ethanol containing a little concentrated hydrochloric acid to give 1-(2'-aminoethyl)-3-hydroxypyrid4-one in 34% yield as colourless needles, m.p. 264°–266° C., $\nu_{max}$ (nujol) 1505, 1540, 1600, 1635 cm$^{-1}$, $\delta(d_6DMSO)$, 2.85 (t, 2H), 4.35 (t, 2H), 7.1 (d, 1H), 8.1 (m, 2H).

EXAMPLE 2

The Ability of Iron Complexes to Donate Iron to Apotransferrin

Apotransferrin ($10^{-4}M$) and the iron complex of 1-ethyl-3-hydroxy-6-hydroxymethylpyrid-4-one ($10^{-4}M$; prepared as described in Example 1) were incubated together in tris hydrochloride (50 mM, buffered to pH 7.4) at 37° C. for 10 minutes when a 1 ml aliquot was removed from the medium and added to a PD10 column. 0.5 ml fractions were collected directly into scintillation vials for counting. The $^{59}Fe$ associated with both the apotransferrin and the ligand was estimated and it was found that over 45% of the iron was removed from the iron complex. A similar value was obtained with the complex of 3-hydroxy-1-(2'-hydroxyethyl)-2-methylpyrid-4-one but with the complex of 1-acetyl-3-hydroxypyrid-2-one over 80% of the iron was removed within 10 minutes.

EXAMPLE 3

In Vitro Tests on Permeation of Iron Complexes into Human Erythrocytes

The accumulation of iron by human erythrocytes which are associated with iron complexes of various of the compounds referred to in Example 1 was studied by incubating for 1 hour at 37° C. a 5% suspension of erythrocytes in a medium consisting of the $^{59}Fe$ labelled iron complex ($10^{-3}M$) in aqueous sodium chloride (130 mM) buffered to pH 7.4 by tris hydrochloride (2 ml) (the iron complex was prepared in situ by an analogous procedure to that described in Example 1). Following this period of incubation, an aliquot of the erythrocyte/medium mixture was placed above a layer of silcone oil and the erythrocytes separated by centrifugation through the oil. The $^{59}Fe$ levels associated with the erythrocytes and the incubation medium were then counted. The results obtained are shown in Table 2 where the amount of the complex entering erythrocytes (n.mole) is given, the quoted values being in each case the mean of at least three determinations.

It will be seen that the uptake of the complexes after 1 hour shows a clear relationship with their $K_{part}$ values quoted in Example 1 except in the case of 1-ethoxycarbonylmethyl-3-hydroxypyrid-2-one. The extremely low uptake of the charged complexes of 1-(2'-aminoethyl)-3-hydroxy-2-methylpyrid-4-one and 1-carboxymethyl-3-hydroxy-2-methylpyrid-4-one reflects their low $K_{part}$ values. The abnormal uptake shown by the complex containing an ester group is probably associated with the extreme lability of the ester bond when the 3-hydroxypyridone is co-ordinated to iron.

TABLE 2

| Uptake of complexes by erythrocytes | |
|---|---|
| Compound | Amount of complex entering erythrocytes (n.mole) |
| Fe$^{III}$ complex of: | |
| 1-acetyl-3-hydroxypyrid-2-one | 240 |
| 1-ethoxycarbonylmethyl-3-hydroxypyrid-2-one | 10 |
| 1-carboxymethyl-3-hydroxypyrid-2-one | <5 |
| 3-hydroxy-1-methyoxycarbonylmethylpyrid-2-one | 230 |
| 3-hydroxy-1-[N—(2'-methylethyl)-carbamoylmethyl]-pyrid-2-one | 52 |
| 1-(N—butylcarbamoylmethyl)-3-hydroxypyrid-2-one | 105 |
| 3-hydroxy-1-(2'-hydroxyethyl)-2-methylpyrid-4-one | <5 |
| 3-hydroxy-1-(3'-hydroxypropyl)-2-methylpyrid-4-one | 30 |
| 3-hydroxy-1-(4'-hydroxybutyl)-2-methylpyrid-4-one | 40 |
| 3-hydroxy-1-(5'-hydroxypentyl)-2-methylpyrid-4-one | 44 |
| 1-carboxymethyl-3-hydroxy-2-methylpyrid-4-one | <5 |
| 1-(2'-carboxyethyl)-3-hydroxy-2-methylpyrid-4-one | 19 |
| 3-hydroxy-1-(2'-methoxycarbonylethyl)-2-methylpyrid-4-one | 25 |
| 1-(2'-aminoethyl)-3-hydroxy-2-methylpyrid-4-one | <5 |

TABLE 2-continued
Uptake of complexes by erythrocytes

| Compound | Amount of complex entering erythrocytes (n.mole) |
|---|---|
| 3-hydroxy-6-hydroxymethyl-1-methylpyrid-4-one | <5 |
| 1-ethyl-3-hydroxy-6-hydroxymethylpyrid-4-one | 26 |

EXAMPLE 4
In Vitro Tests on Permeation of Rat Jejunal Sac by Iron Complexes

The iron uptake into the serosal space of the inverted rat jejunal sac was compared for the iron complexes of various of the compounds referred to in Example 1. Rats (male Sprague Dawley, 60 g) were killed and the jejunum removed, everted and cut into three segments (4 cm length). The segments were tied at both ends and filled with Krebs Ringer buffer (0.2 ml) and incubated in Krebs Ringer buffer containing $^{59}$Fe complexes at 37° C. for periods up to 1 hour (the iron complex was prepared in situ by an analogous procedure to that described in Example 1). The contents of the sac were counted for $^{59}$Fe and measured spectrophotometrically.

The results obtained for various iron complexes according to the present invention and, by way of comparison, for seven other iron compounds which are each contained in preparations marketed for the treatment of iron deficiency anaemia are shown in Table 3, the iron uptake for each compound being shown relative to that for ferric chloride as 1. It will be seen that the complexes of Example 1 each provide a level of iron uptake which is significantly higher than the levels observed for any of the 7 compounds in current use for the treatment or iron deficiency anaemia.

TABLE 3

| Compound | Relative Iron Uptake |
|---|---|
| FeCl$_3$ | 1 |
| Fe$^{III}$ complex of: | |
| 1-acetyl-3-hydroxypyrid-2-one | 38 |
| 1-ethoxycarbonylmethyl-3-hydroxypyrid-2-one | 26 |
| 1-carboxymethyl-3-hydroxypyrid-2-one | 11 |
| 3-hydroxy-1-methoxycarbonylmethylpyrid-2-one | 31 |
| 1-(N—ethylcarbamoylmethyl)-3-hydroxypyrid-2-one | 23 |
| 3-hydroxy-1-(N—methylcarbamoylmethyl)-pyrid-2-one | 24 |
| 3-hydroxy-1-(N—propylcarbamoylmethyl-pyrid-2-one | 18 |
| 3-hydroxy-1-(3'-hydroxypropyl)-2-methylpyrid-4-one | 16 |
| 3-hydroxy-1-(4'-hydroxybutyl)-2-methylpyrid-4-one | 30 |
| 1-(5'-acetoxypentyl)-3-hydroxy-2-methylpyrid-4-one | 33 |
| 1-carboxymethyl-3-hydroxy-2-methylpyrid-4-one | 13 |
| 1-(2'-carboxyethyl)-3-hydroxy-2-methylpyrid-4-one | 29 |
| 1-(2'-aminoethyl)-3-hydroxy-2-methylpyrid-4-one | 18 |
| Fe$^{II}$ sulphate | 2.4 |
| Fe$^{II}$ fumarate | 4.0 |
| Fe$^{II}$ gluconate | 1.6 |
| Fe$^{II}$ succinate | 2.0 |
| Fe$^{III}$ EDTA | 3.6 |
| Fe$^{III}$ ascorbate | 0.4 |
| Fe$^{III}$ citrate | 2.0 |

We claim:

1. A method for increasing the level of iron in the blood stream of a patient in need of such treatment which comprises administering to said patient an amount sufficient to elicit such an effect of a ferric iron complex of a 3-hydroxypyrid-2-one or 3-hydroxypyrid-4-one compound in which the hydrogen atom attached to the nitrogen atom is replaced by an acyclic or cyclic aliphatic carboxylic acid acyl group or by an acyclic or cyclic aliphatic hydrocarbon group which can further be substituted by one or two substituents selected from acyclic or cyclic aliphatic carboxylic acid acyl, acyclic or cyclic alkoxy, acyclic or cyclic aliphatic amido, halo and hydroxy groups, and acyclic or cyclic aliphatic hydrocarbylcarbonyloxy, hydrocarbylsulphonyloxy, hydrocarbyloxycarbonyl and hydrocarbyloxysulphonyl moieties, but excluding substitution by two hydroxy groups, and wherein one or more of the hydrogen atoms attached to ring carbon atoms can be replaced by one of said substituents or by an acyclic or cyclic aliphatic hydrocarbon group which can further be substituted by an acyclic or cyclic alkoxy, halo or hydroxy group, or an acyclic or cyclic aliphatic hydrocarbylcarbonyloxy, hydrocarbylsulphonyloxy, hydrocarbyloxycarbonyl or hydrocarbyloxysulphonyl moiety, but excluding compounds in which said replacement of hydrogen atoms in the compound is effected only by unsubstituted acyclic or cyclic aliphatic hydrocarbon groups, wherein said compound when metal free has a partition coefficient between n-octanol and 20 mM tris hydrochloride, pH 7.4, of between 0.02 and 3.0 for the ratio (concentration of compound in organic phase)/(concentration of compound in aqueous phase).

2. The method according to claim 1, in which any replacement of a hydrogen atom attached to a ring carbon atom is effected by a C$_{1-4}$ acyclic or cyclic aliphatic hydrocarbon group.

3. A neutral 3:1 hydroxypyridone:iron(III) complex of 3-hydroxypyrid-2-one, 3-hydroxypyrid-4-one, 2-methyl-3-hydroxypyrid-4-one, 6-methyl-3-hydroxypyrid-4-one or 2,6-dimethyl-3-hydroxypyrid-4-one with the hydrogen atom attached to the nitrogen atom replaced by an acyclic aliphatic carboxylic acid acyl group —COR$_1$, an acyclic aliphatic hydrocarbon group —(CH$_2$)$_n$— carrying a terminal substituent group —COR$_1$, —COXR$_1$, —SO$_2$XR$_1$, —XCOR$_1$ or —XSO$_2$R$_1$, or an acyclic aliphatic hydrocarbon group —(CH$_2$)$_m$— carrying a terminal substituent group —OH, wherein R$_1$ is a C$_{1-4}$ acyclic aliphatic hydrocarbon group, X is an oxy or imino group, n is an integer from 1 to 6, and m is an integer from 2 to 6.

4. The method according to claim 1, in which the 3-hydroxypyridone compound is substituted only on the nitrogen atom or is substituted on the nitrogen atom and on one of the ring carbon atoms.

5. A pharmaceutical composition comprising:
(a) a ferric iron complex of a 3-hydroxypyrid-2-one or 3-hydroxypyrid-4-one compound in which the hydrogen atom attached to the nitrogen atom is replaced by an acyclic or cyclic aliphatic carboxylic acid acyl group or by an acyclic or cyclic aliphatic hydrocarbon group which can further be substituted by one or two substituents selected from acyclic or cyclic aliphatic carboxylic acid acyl, acyclic or cyclic alkoxy, acyclic or cyclic aliphatic amido, halo and hydroxy groups, and acyclic or cyclic aliphatic hydrocarbylcarbonyloxy, hydrocarbylsulphonyloxy, hydrocarbyloxycarbonyl and hydrocarbyloxysulphonyl moieties, but excluding substitution by two hydroxy groups, and wherein one or more of the hydrogen atoms attached to ring carbon atoms can be replaced by one of said substituents or by an acyclic or cyclic aliphatic hydrocarbon group which can be further substituted by an acyclic or cyclic alkoxy, halo or hydroxy group, or an acyclic or cyclic aliphatic hydrocarbylcarbonyloxy, hydrocarbylsulphonyloxy, hydrocarbyloxycarbonyl or hydrocarbyloxysulphonyl moiety, but excluding compounds in which said replacement of hydrogen atoms in the compound is effected only by unsubstituted acyclic or cyclic aliphatic hydrocarbon groups and also excluding the compound 3-hydroxy-6-hydroxymethyl-1-methylpyrid-4-one, wherein said compound when metal free has a partition coefficient between n-octanol and 20 mM tris hydrochloride, pH 7.4, of between 0.02 and 3.0 for the ratio (concentration of compound in organic phase)/(concentration of compound in aqueous phase); and (b) a physiologically acceptable diluent or carrier.

6. The pharmaceutical composition according to claim 5, in which the hydrogen atoms attached to ring carbon atoms either are not replaced or are replaced by an aliphatic hydrocarbon group which is an acyclic alkyl group of 1 to 4 carbon atoms.

7. The method according to claim 1, in which the iron complex is the neutral 3:1 hydroxypyridone: iron(III) complex.

8. The pharmaceutical composition according to claim 5, which is adapted for oral administration.

9. The pharmaceutical composition according to claim 5, which additionally contains folic acid.

10. A method for increasing the level of iron in the blood stream of a patient in need of such treatment which comprises administering to said patient an amount sufficient to elicit such an effect of a neutral 3:1 hydroxypyridone:iron(III) complex of a 3-hydroxypyrid-2-one or 3-hydroxypyrid-4-one compound in which the nitrogen atom is substituted by a $C_{2-5}$ acylic or cyclic aliphatic hydrocarbon group substituted by a single substituent selected from $C_{2-5}$ acylic or cyclic alkylcarbonyl, $C_{1-4}$ acylic or cyclic alkoxy, halo, hydroxy and unsubstituted or $C_{1-4}$ acylic or cyclic alkyl mono- or di-substituted amido groups, and $C_{1-4}$ acylic or cyclic alkylcarbonyloxy, alkylsulphonyloxy, alkoxycarbonyl and alkoxysulphonyl moieties and one or more of the ring carbon atoms can further be substituted by a $C_{1-4}$ acylic or cyclic aliphatic hydrocarbon group.

11. The pharmaceutical composition according to claim 5, in which the iron complex is in substantially pure form.

12. The pharmaceutical composition according to claim 5, which additionally contains an iron chelating agent selected from the group consisting of (1) 3-hydroxypyrid-2-one and 3-hydroxypyrid-4-one compounds in which the hydrogen atom attached to the nitrogen atom is replaced by an acyclic or cyclic aliphatic hydrocarbon group and in which one or more of the hydrogen atoms attached to ring carbon atoms can be replaced by an acyclic or cyclic aliphatic hydrocarbon group and salts thereof containing a physiologically acceptable cation and (2) 3-hydroxypyrid-2-one and 3-hydroxypyrid-4-one compounds as defined in claim 5 and salts thereof containing a physiologically acceptable cation.

13. The pharmaceutical composition according to claim 12, in which the iron chelating agent is the same hydroxypyridone as in the iron complex, or a salt thereof containing a physiologically acceptable cation in uncomplexed form.

14. The pharmaceutical composition according to claim 13, in which the molar proportion of uncomplexed hydroxypyridone:iron complex is from 1:1 to 10:1.

15. A pharmaceutical composition according to claim 5, in which the diluent is water or a medium containing an organic solvent and the composition has the form of a solution, suspension or emulsion.

16. The pharmaceutical composition according to claim 15, in which said diluent consists in whole or in part of a glycol.

17. The pharmaceutical composition according to claim 15, in sterile injectable form.

18. The pharmaceutical composition according to claim 5, in which the carrier is a physiologically acceptable solid carrier.

19. The pharmaceutical composition according to claim 18 in tablet or capsule form.

20. The pharmaceutical composition according to claim 5 in delayed release form.

21. The pharmaceutical composition according to claim 5 which is adapted to release of the iron complex in the intestine rather than in the stomach.

22. The pharmaceutical composition according to claim 21, in which the iron complex is encapsulated by a material resistant to dissociation under acidic aqueous conditions.

23. The pharmaceutical composition according to claim 22, in which the iron complex is encapaulated by a solid material which is resistant to dissociation under acidic aqueous conditions but which is adapted for dissociation under non-acidic aqueous conditions.

24. A pharmaceutical composition according to claim 5 in unit dosage form.

25. A ferric iron complex of a 3-hydroxypyrid-2-one or 3-hydroxypyrid-4-one compound in which the hydrogen atom attached to the nitrogen atom is replaced by an acyclic or cyclic aliphatic carboxylic acid acyl group or by an acyclic or cyclic aliphatic hydrocarbon group which can further be substituted by one or two substituents selected from acyclic or cyclic aliphatic carboxylic acid acyl, acyclic or cyclic alkoxy, acyclic or cyclic aliphatic amido, halo and hydroxy groups, and acyclic or cyclic aliphatic hydrocarbylcarbonyloxy, hydrocarbylsulphonyloxy, hydrocarbyloxycarbonyl and hydrocarbyloxysulphonyl moieties, but excluding substitution by two hydroxy groups, and wherein one or more of the hydrogen atoms attached to ring carbon atoms can be replaced by one of said substituents or by an acyclic or cyclic aliphatic hydrocarbon group which can be further substituted by acyclic or cyclic alkoxy, halo or hydroxy groups, or an acyclic or cyclic aliphatic hydrocarbylcarbonyloxy, hydrocarbylsulphonyloxy, hydrocarbyloxycarbonyl or hydrocarbyloxysulphonyl moiety, but excluding compounds in which said replacement of hydrogen atoms in the compound is effected only by unsubstituted acyclic or cyclic aliphatic hydrocarbon groups, and also excluding the compound 3-hydroxy-6-hydroxymethyl-1-methylpyrid-4-one, wherein said compound when metal free has a partition coefficient between n-octanol and 20 mM tris hydrochloride, pH 7.4, of between 0.02 and 3.0 for the ratio (concentration of compound in organic phase)/(concentration of compound in aqueous phase).

26. The ferric complex according to claim 25, in which any replacement of a hydrogen atom attached to a ring carbon atom is effected by a $C_{1-4}$ acyclic or cyclic aliphatic hydrocarbon group.

27. The complex according to claim 25, in which the 3-hydroxypyridone compound is substituted only on the nitrogen atom or is substituted on the nitrogen atom and one one of the ring carbon atoms.

28. A neutral 3:1 hydroxypyridone:iron(III) complex of 3-hydroxypyrid-2-one, 3-hydroxypyrid-4-one or a 2-alkyl-3-hydroxypyrid-4-one, 6-alkyl-3-hydroxypyrid-4-one or 2,6-dialkyl-3-hydroxypyrid-4-one, the alkyl groups being acylic or cyclic, with the hydrogen atom attached to the nitrogen atom replaced by a $C_{2-5}$ acylic or cyclic alkylcarbonyl group or by a $C_{1-6}$ acylic or cyclic aliphatic hydrocarbon group substituted by a single substituent selected from $C_{2-5}$ acylic or cyclic alkylcarbonyl, $C_{1-4}$ acylic or cyclic alkoxy, halo, hydroxy, and unsubstituted or $C_{1-4}$ acylic or cyclic alkyl mono- or di-substituted amido groups, and $C_{1-4}$ acylic or cyclic alkylcarbonyloxy, alkylsulphonyloxy, alkoxycarbonyl and alkoxysulphonyl moieties.

29. The ferric complex according to claim 28, in which the alkyl group or groups at the 2-, 6-, or 2- and 6-positions of the 3-hydroxypyridone are $C_{1-3}$ acyclic groups.

30. The complex according to claim 3, in which the nitrogen atom of the 3-hydroxypyridone compound is substituted by a group $-(CH_2)_n-COXR_1$ wherein $-(CH_2)_n-$ and $R_1$ together contain 3 to 7 carbon atoms.

31. The ferric complex according to claim 3, in which $R_1$ and $R_2$ are each an acyclic alkyl group of 1 to 4 carbon atoms, n is an integer from 1 to 4 with the number of carbon atoms in $-(CH_2)_n-$ and $R_1$ being 3 to 7 carbon atoms, and m is an integer from 3 to 6.

32. The ferric complex according to claim 25, in which the hydroxypyridone is a 3-hydroxypyrid-2-one N-substituted by a group $-(CH_2)_nCOXR_1$ or a 3-hydroxy-2-methylpyrid-4-one N-substituted by a group $-(CH_2)_nCOXR_1$ or $-(CH_2)_mXH$ wherein $R_1$ is a acyclic alkyl group of 1 to 4 carbon atoms, X is an oxy group, n is an integer from 1 to 4 with the number of carbon atoms in $-(CH_2)_n-$ and $R_1$ being 3 to 7 carbon atoms, and m is an integer from 3 to 6.

33. The ferric complex according to claim 25, in which the hydrogen atom attached to the nitrogen atom is replaced by an acyclic or cyclic aliphatic hydrocarbon group and the hydrogen atom attached to a ring carbon atom at the 6-position is replaced by an acyclic or cyclic alkoxymethyl, halomethyl, or hydroxymethyl group.

34. The ferric complex according to claim 33, in which the aliphatic hydrocarbon group is an acyclic alkyl group of 1 to 4 carbon atoms.

35. The ferric complex according to claim 25, in which the ferric complex is the neutral 3:1 hydroxypyridone:iron(III) complex.

36. The pharmaceutical composition according to claim 30, in which the neutral 3:1 complex is substantially free from complexes containing other proportions of the hydroxypyridone and iron.

37. A method for increasing the level of iron in the bloodstream of a patient in need of such treatment which comprises administering to said patient an amount sufficient to elicit such an effect of a neutral 3:1 hydroxypyridone:iron(III) complex of 3-hydroxypyrid-2-one, 3-hydroxypyrid-4-one, 3-hydroxy-2-methylpyrid-4-one, 3-hydroxy-6-methylpyrid-4-one or 3-hydroxy-2,6-dimethylpyrid-4-one with the hydrogen atom attached to the nitrogen atom replaced by an acyclic aliphatic carboxylic acid acyl group $-COR_1$, an acyclic aliphatic hydrocarbon group $-(CH_2)_n-$ carrying a terminal substituent group $-COR_1$, $-COXR_1$, $-SO_2XR_1$, $-XCOR_1$ or $-XSO_2R_1$, or an acyclic aliphatic hydrocarbon group $-(CH_2)_m-$ carrying a terminal substituent group $-OH$, wherein $R_1$ is a $C_{1-4}$ acyclic alkyl group, X is an oxy or imino group, n is an integer from 1 to 4 and m is an integer from 3 to 6.

38. A pharmaceutical composition comprising:
(a) a neutral 3:1 hydroxypyridone:iron(III) complex of a 3-hydroxypyrid-2-one or 3-hydroxypyrid-4-one compound in which the nitrogen atom is substituted by a $C_{2-5}$ acylic or cyclic aliphatic hydrocarbon group substituted by a single substituent selected from $C_{2-5}$ acylic or cyclic alkylcarbonyl, $C_{1-4}$ acylic or cyclic alkoxy, halo, hydroxy, and unsubstituted or $C_{1-4}$ acylic or cyclic alkyl mono- or di-substituted amido groups, and $C_{1-4}$ acylic or cyclic alkylcarbonyloxy, alkylsulphonyloxy, alkoxycarbonyl and alkoxysulphonyl moieties, and one or more of the ring carbon atoms can further be substituted by a $C_{1-4}$ acylic or cyclic aliphatic hydrocarbon group; and
(b) a physiologically acceptable diluent or carrier.

39. A pharmaceutical composition comprising:
(a) a neutral 3:1 hydroxypyridone:iron(III) complex of 3-hydroxypyrid-2-one, 3-hydroxypyrid-4-one, 3-hydroxy-2-methylpyrid-4-one, 3-hydroxy-6-methylpyrid-4-one or 3-hydroxy-2,6-dimethylpyrid-4-one with the hydrogen atom attached to the nitrogen atom replaced by an acyclic aliphatic carboxylic acid acyl group $-COR_1$, an acyclic aliphatic hydrocarbon group $-(CH_2)_n-$ carrying a terminal substituent group $-COR_1$, $-COXR_1$, $-SO_2XR_1$, $-XCOR_1$ or $-XSO_2R_1$, or an acyclic aliphatic hydrocarbon group $-(CH_2)_m-$ carrying a terminal substituent group $-XH$, wherein $R_1$ is a $C_{1-4}$ acyclic alkyl group, X is an oxy or imino group, n is an integer from 1 to 4 and m is an integer from 3 to 6; and
(b) a physiologically acceptable diluent or carrier.

40. The pharmaceutical composition according to claim 5, in which the iron complex is the neutral 3:1 hydroxypyridone:iron(III) complex.

41. The ferric complex according to claim 29, in which the acyclic alkyl groups are methyl.

* * * * *